US009862777B2

(12) United States Patent
Robberecht et al.

(10) Patent No.: US 9,862,777 B2
(45) Date of Patent: Jan. 9, 2018

(54) SINGLE DOMAIN ANTIBODIES AGAINST SOD1 AND THEIR USE IN MEDICINE

(71) Applicants: VIB VZW, Ghent (BE); Life Sciences Research Partners VZW, Leuven (BE); Katholieke Universiteit Leuven, K.U.Leuven R&D, Leuven (BE)

(72) Inventors: Wim Robberecht, Kumtich (BE); Frederic Rousseau, Sint-Martens-Bodegem (BE); Joost Schymkowitz, Meensel-Kiezegem (BE)

(73) Assignees: VIB VZW, Ghent (BE); LIFE SCIENCES RESEARCH PARTNERS VZW, Leuven (BE); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 0 days.

(21) Appl. No.: 14/894,980

(22) PCT Filed: May 28, 2014

(86) PCT No.: PCT/EP2014/061129
§ 371 (c)(1),
(2) Date: Nov. 30, 2015

(87) PCT Pub. No.: WO2014/191493
PCT Pub. Date: Dec. 4, 2014

(65) Prior Publication Data
US 2016/0115245 A1 Apr. 28, 2016

(30) Foreign Application Priority Data

May 28, 2013 (EP) .................................... 13169476

(51) Int. Cl.
*C07K 16/40* (2006.01)
*A61K 39/395* (2006.01)
*A61K 39/00* (2006.01)

(52) U.S. Cl.
CPC ........ *C07K 16/40* (2013.01); *A61K 2039/505* (2013.01); *C07K 2317/22* (2013.01); *C07K 2317/569* (2013.01); *C07K 2317/76* (2013.01); *C07K 2317/77* (2013.01); *C07K 2317/92* (2013.01); *C07K 2319/21* (2013.01); *C07K 2319/41* (2013.01); *C07K 2319/42* (2013.01)

(58) Field of Classification Search
None
See application file for complete search history.

(56) References Cited

U.S. PATENT DOCUMENTS

2007/0292410 A1* 12/2007 Cashman .......... A61K 31/7088
424/130.1
2014/0044722 A1 2/2014 Ambrosino et al.

FOREIGN PATENT DOCUMENTS

| WO | 2012058220 | 5/2012 |
|----|-----------|--------|
| WO | 2014191493 | 12/2014 |
| WO | 2012080518 | 6/2015 |

OTHER PUBLICATIONS

PCT International Search Report dated Sep. 5, 2014, PCT/EP2014/061129.
Francois Gros-Louis et al., Intracerebroventricular infusion of monoclonal antibody or its derived Fab fragment against misfolded forms of SOD1 mutant delays mortality in a mouse model of ALS, Journal of Neurochemisty, Jun. 1, 2010, pp. 1188-1199, vol. 113, No. 5, Wiley Interscience.
Hsueh-Ning Liu et al., Targeting of Monomer/Misfolded SOD1 as a Therapeutic Strategy for Amyotrophic Lateral Sclerosis, The Journal of Neuroscience, Jun. 27, 2012, pp. 8791-8799, vol. 32, No. 26.
Miller et al., Intrabody Applications in Neurological Disorders: Progress and Future Prospects, Molecular Therapy, Sep. 1, 2005, pp. 394-401, vol. 12, No. 3, Nature Publishing Group.
Urushitani Makoto, Antibody therapy targeting ALS-linked misfolded protein, Rinsho Shinkeigaku = Clinical Neurology, Nov. 2011, pp. 1162-1164, vol. 51, No. 11.
Hernandez et al., Nanobody against SOD1 reduces In vitro aggregation, rescues SOD1 induced axonopathy and extends survival in ALS models, Society for Neuroscience Abstract Viewer and Itinerary Planner, 2013, vol. 43.
Daryl Bosco et al., Wild-type and mutant SOD1 share an aberrant conformation and a common pathogenic pathway in ALS, Nature Neuroscience, Nov. 1, 2010, pp. 1396-1403, vol. 13, No. 11, Nature America, Inc.
Takao Fujisawa et al., A Novel Monoclonal Antibody Reveals a Conformational Alteration Shared by Amyotrophic Lateral Sclerosis-Linked SOD1 Mutants, Annals of Neurology, Nov. 27, 2012, pp. 739-749, vol. 72, No. 5.
Karin Forsberg et al., Novel Antibodies Reveal Inclusions Containing Non-Native SOD1 in Sporadic ALS Patients, PLOS one, Jul. 14, 2010, pp. e11552, vol. 5, issue 7.
Dirk Saerens et al., Single-Domain antibodies as building blocks for novel therapeutics, Current Opinion in Pharmacology, Oct. 1, 2008, pp. 600-608, vol. 8, No. 5, Elsevier Science Publishers.
Erwin De Genst et al., Nanobodies as Structural Probes of Protein Misfolding and Fibril Formation, Methods in Molecular Biology, 2012, pp. 533-558, vol. 911.
Marka van Blitterswijk et al., Anti-superoxide dismutase antibodies are associated with survival in patients with sporadic amyotrophic lateral sclerosis, Amyotrophic Lateral Sclerosis, Nov. 1, 2011, pp. 430-438, vol. 12, No. 6.

* cited by examiner

Primary Examiner — Kimberly A. Ballard
Assistant Examiner — Stacey MacFarlane
(74) Attorney, Agent, or Firm — TraskBritt, P.C.

(57) ABSTRACT

The present application relates to the field of single-domain antibodies (also called nanobodies), more particularly single-domain antibodies against SOD1 protein isoforms. It also relates to the use of these nanobodies in medicine. Accordingly, methods to treat a disease using these nanobodies are provided herein. The single-domain antibodies are particularly envisaged for treatment of ALS.

15 Claims, 17 Drawing Sheets

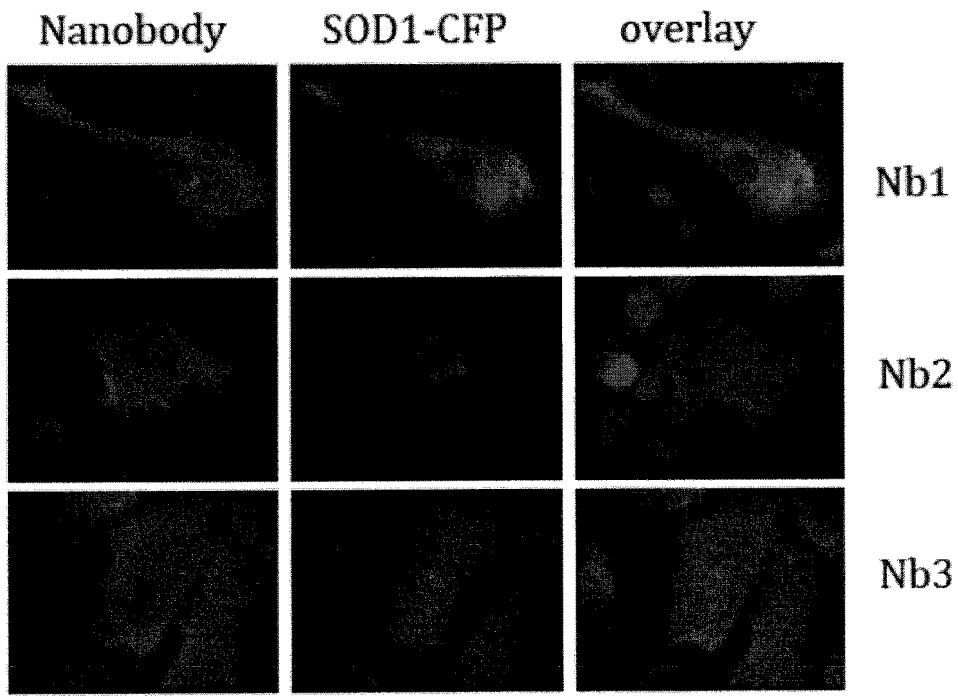
FIG. 2A
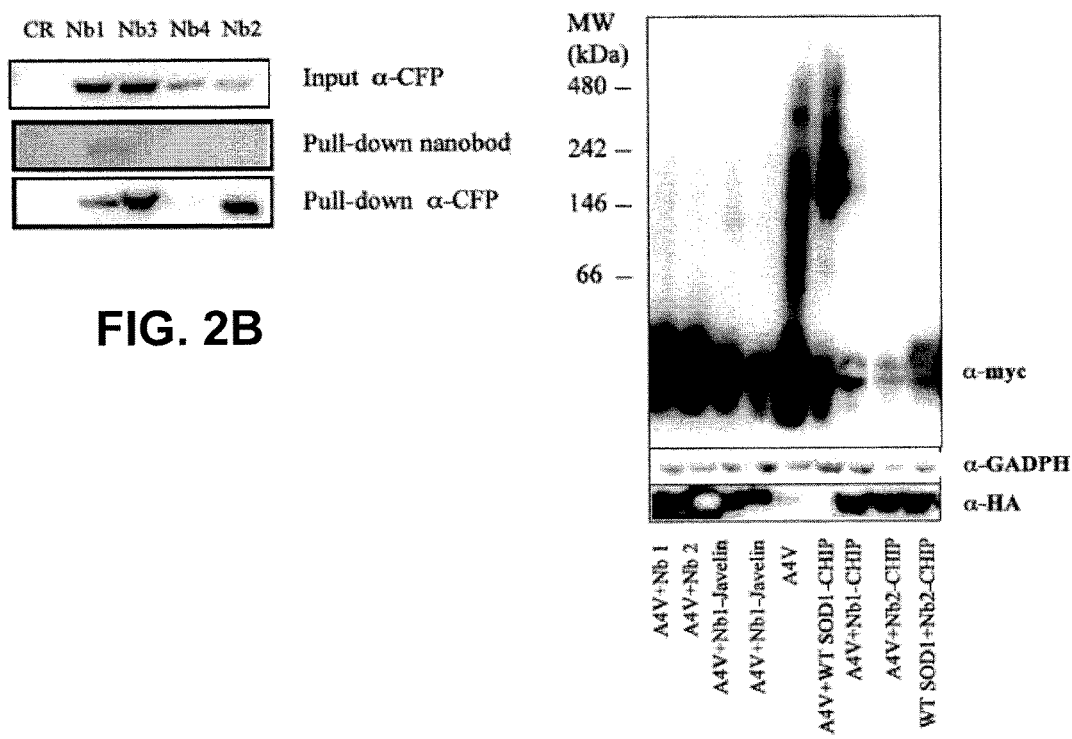
FIG. 2B
FIG. 2C

1. Non transfected
2. CTL NB
3. SOD1 NB

FIG. 5A  FIG. 5B

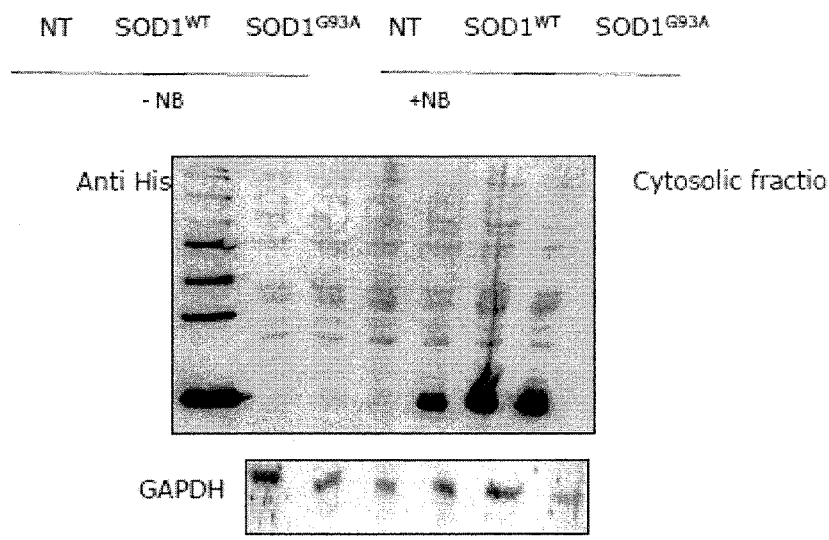
FIG. 8A
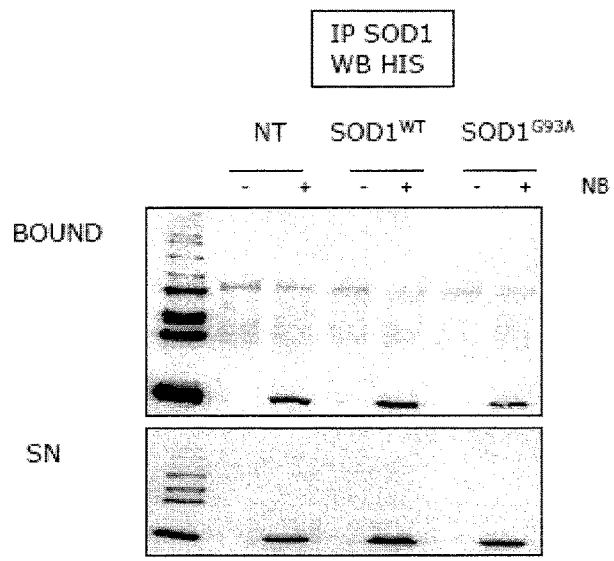
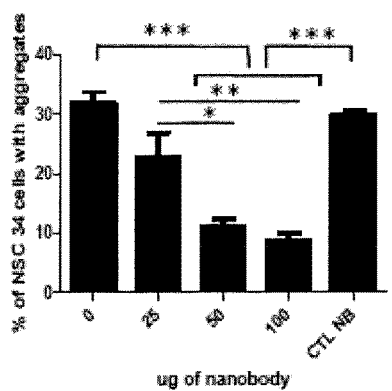
FIG. 8C
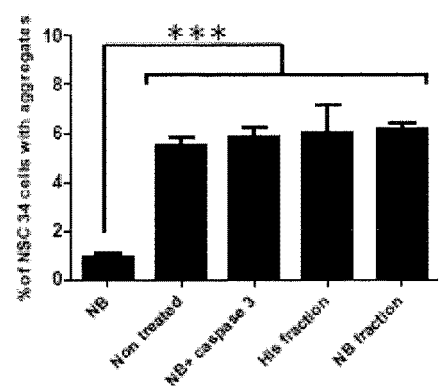
FIG. 8D
FIG. 8B

Effect of SOD1 nanobody (protein) on axonal length 24 hours after NB administration (water)

FIG. 11C  FIG. 11E

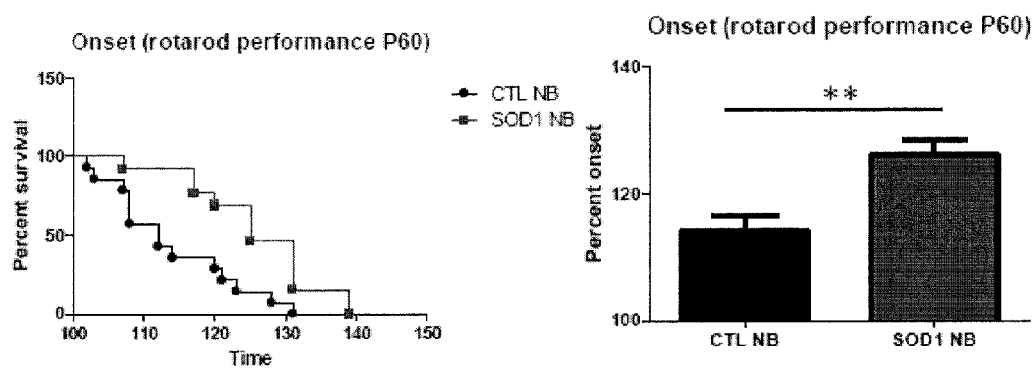
FIG. 12D
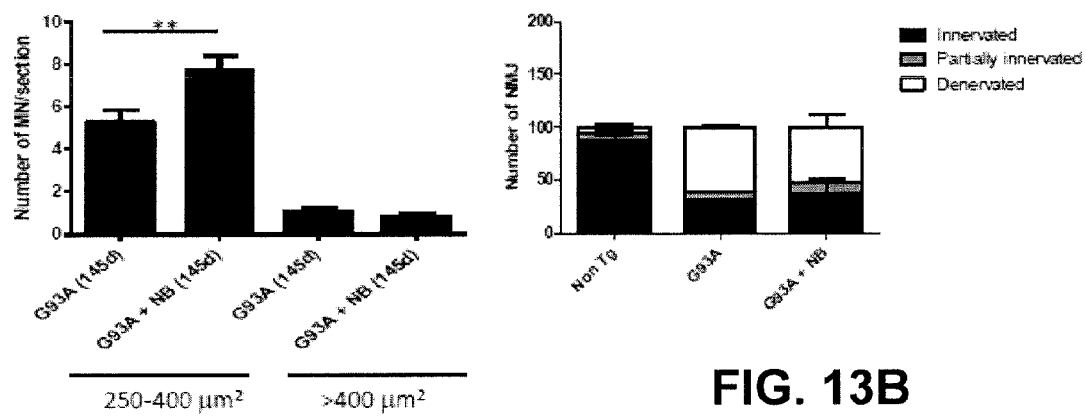
FIG. 13A
FIG. 13B
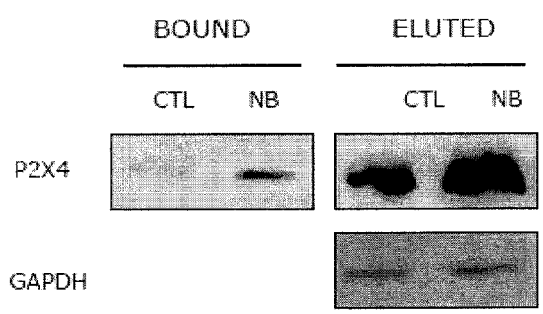
FIG. 14

| | | |
|---|---|---|
| Nb3: | QVQLQESGGGLVQAGGSLRLSCAASG----LPYRTVFMGWFRQGPGKEREGVAVINADGVST-YYADSVKGRFTISQDNAKNTVYLQMNSLKPEDTAIYHCAANHFPDYSRDPLATAEYNYWGQ | 119 |
| 4SD-29: | QVQLQESGGGSVQAGGSLRLSCAASG----LPYRTVFMGWFRQGPGKEREGVAVINADGVST-YYADSVKGRFTISRDNAKDTYLQMNSLKPEDTAIYHCAANHFPDYSRDPLATAEYNYWGQ | 119 |
| 4SD-7: | QVQLQESGGGSVQAGGSLRLSCAASG----LPYRTVFMGWFRQGPGKEREGVAVINADGVST-YYADSVKGRFTISQDNAKNTVYLQMNSLKPEDTAIYHCAANHFPDYSRDPLATAEYNYWGQ | 119 |
| RSO-R2-14: | QVQLQESGGGSVQAGGSLRLSCAAPG----LPYRVVFMGWFRQGPGKEREGVAVINADGVST-YYADSVKGRFTISQDNAKNTVYLQMNSLKPEDTAIYCAANHFPDYSRDPLATAEYNYWGQ | 119 |
| 4SD34: | QVQLQESGGGSVQAGGSLRLACVASGDTRPYITYWMGWYRQAPGKEREGVATIYTGGSGT-YYSDSVEGRFTISQDNAQRTVYLQMNDLKPEDGMYYCAAGNGALPPGRRLSPQNMDTWGP | 122 |
| Nb2: | QVQLQESGGGSVQAGGSLRLACVASGDTRPYITYWMGWYRQAPGKEREGVATIYTGGSGT-YYSDSVEGRFTISQDKGAQRTVYLQMNDLKPEDTAMYYCAAGNGALPPGRRLSPQNMDTWGP | 122 |
| Nb4: | QVQLQESGGGSVQTGGSLRLSCAASG----YTPSSYCMGWFRQAPGKEREGRELVSTIISDG-ST-YYADSVKGRFTISQDNAKNTVYLQMNEKAEDTAIYYCAARSGGVCSG---RASRYNYWGQ | 115 |
| 4S10: | QVQLQESGGGLVQPGGSLRLSCRASES----LFSLYAMGWYRQAPGKQPELIATISGGGEGTGNYADPVKGRFTISRNNANNMVFLQMNSLKPEDTAVYYCNVYG---------TNLAPWGQ | 109 |
| 4S-37: | QVQLQESGGGLVQPGGSLRLSCRASET----LFSLYAMGWYRQAPGKQPELIATISGGGEGTGNYADPVKGRFTISRNNANNMVFLQMNNLKPEDTAVYYCNVYG---------TNLAPWGQ | 109 |
| Nb1: | QVQLQESGGGLVQPGGSLRLSCRASET----LFSLYAMGWYRQAPGKQPELIATISGGGEGTGNYADPVKGRFTISRNNADNMVFLQMNLKPEDTAVYYCNVYG---------TNLAPWGQ | 109 |
| 4SP-4: | QVQLQESGGGLVQPGGSLRLSCRVSES----LFSLYAMGWYRQAPGKQPELIATISGGGEGTGNYADPVKGRFTISRNNANNTVFLQMNSLKPEDTAVYYCNVYG---------TNLAPWGQ | 109 |
| 4SP-9: | QVQLQESGGGLVQPGGSLRLSCRASES----LFSLYAMGWYRQAPGKQPELIATISGGGEGTGNYADPVKGRFTISRNNANNTVFLQMNSLKPEDTAVYYCNVYG---------TNLAPWGQ | 109 |
| 4SP-19: | QVQLQESGGGLVQPGGSLRLSCAASET----LFSLYAMGWYRQAPGKQPELIATISGGGEGTGNYADPVKGRFTISRNGDNMVFLQMNNLKPEDTAVYYCNVYG---------TNLAPWGQ | 109 |
| 4S16: | QVQLQESGGGLVHSGGSLRLSCRVSES----LFSLYAMGWYRQALGKQPELIATISGGGEGTGNYADPVKGRFTISRNNANNTVFLQMNSLKPEDTAVYYCNVYG---------TNLAPWGQ | 109 |

| | |
|---|---|
| Nb3: | GTQVTVSS (SEQ ID NO: 3) |
| 4SD-29: | GTQVTVSS (SEQ ID NO: 5) |
| 4SD-7: | GTQVTVSS (SEQ ID NO: 6) |
| RSO-R2-14: | GTQVTVSS (SEQ ID NO: 7) |
| 4SD34: | GTQVTVSS (SEQ ID NO: 8) |
| Nb2: | GTQVTVSS (SEQ ID NO: 1) |
| Nb4: | GTQVTVSS (SEQ ID NO: 4) |
| 4S10: | GTQVTVSS (SEQ ID NO: 9) |
| 4S-37: | GTQVTVSS (SEQ ID NO: 10) |
| Nb1: | GTQVTVSS (SEQ ID NO: 2) |
| 4SP-4: | GTQVTVSS (SEQ ID NO: 11) |
| 4SP-9: | GTQVTVSS (SEQ ID NO: 12) |
| 4SP-19: | GTQVTVSS (SEQ ID NO: 13) |
| 4S16: | GTQVTVSS (SEQ ID NO: 14) |

FIG. 15

SEQUENCE LISTING

```
<160> NUMBER OF SEQ ID NOS: 28

<210> SEQ ID NO 1
<211> LENGTH: 130
<212> TYPE: PRT
<213> ORGANISM: Camelus dromedarius

<400> SEQUENCE: 1

Gln Val Gln Leu Gln Glu Ser Gly Gly Gly Ser Val Gln Ala Gly Gly
1               5                   10                  15

Ser Leu Arg Leu Ala Cys Val Ala Ser Gly Gly Asp Thr Arg Pro Tyr
            20                  25                  30

Ile Thr Tyr Trp Met Gly Trp Tyr Arg Gln Ala Pro Gly Lys Glu Arg
        35                  40                  45

Glu Gly Val Ala Thr Ile Tyr Thr Gly Gly Ser Gly Thr Tyr Tyr Ser
    50                  55                  60

Asp Ser Val Glu Gly Arg Phe Thr Ile Ser Gln Asp Lys Ala Gln Arg
65                  70                  75                  80

Thr Val Tyr Leu Gln Met Asn Asp Leu Lys Pro Glu Asp Thr Ala Met
                85                  90                  95

Tyr Tyr Cys Ala Ala Gly Asn Gly Ala Leu Pro Pro Gly Arg Arg Leu
            100                 105                 110

Ser Pro Gln Asn Met Asp Thr Trp Gly Pro Gly Thr Gln Val Thr Val
        115                 120                 125

Ser Ser
    130

<210> SEQ ID NO 2
<211> LENGTH: 117
<212> TYPE: PRT
<213> ORGANISM: Vicugna pacos

<400> SEQUENCE: 2

Gln Val Gln Leu Gln Glu Ser Gly Gly Gly Leu Val Gln Pro Gly Gly
1               5                   10                  15

Ser Leu Arg Leu Ser Cys Arg Ala Ser Glu Thr Leu Phe Ser Leu Tyr
            20                  25                  30

Ala Met Gly Trp Tyr Arg Gln Ala Pro Gly Lys Gln Pro Glu Leu Ile
        35                  40                  45

Ala Thr Ile Ser Gly Gly Gly Glu Gly Thr Gly Asn Tyr Ala Asp Pro
    50                  55                  60

Val Lys Gly Arg Phe Thr Ile Ser Arg Asn Asn Ala Asp Asn Met Val
```

```
            65                  70                  75                  80
Phe Leu Gln Met Asn Asn Leu Lys Pro Glu Asp Thr Ala Val Tyr Tyr
                85                  90                  95
Cys Asn Val Tyr Gly Thr Asn Leu Ala Pro Trp Gly Gln Gly Thr Gln
               100                 105                 110
Val Thr Val Ser Ser
            115
```

<210> SEQ ID NO 3
<211> LENGTH: 127
<212> TYPE: PRT
<213> ORGANISM: Camelus dromedarius

<400> SEQUENCE: 3

```
Gln Val Gln Leu Gln Glu Ser Gly Gly Gly Leu Val Gln Ala Gly Gly
1               5                   10                  15
Ser Leu Arg Leu Ser Cys Ala Ala Ser Gly Leu Pro Tyr Arg Thr Val
            20                  25                  30
Phe Met Gly Trp Phe Arg Gln Gly Pro Gly Lys Glu Arg Glu Gly Val
            35                  40                  45
Ala Val Ile Asn Ala Asp Gly Val Ser Thr Tyr Tyr Ala Asp Ser Val
        50                  55                  60
Lys Gly Arg Phe Thr Ile Ser Gln Asp Asn Ala Lys Asn Thr Val Tyr
65                  70                  75                  80
Leu Gln Met Asn Ser Leu Lys Pro Glu Asp Thr Ala Ile Tyr His Cys
                85                  90                  95
Ala Ala Asn His Phe Phe Asp Tyr Ser Arg Asp Pro Leu Ala Thr Ala
               100                 105                 110
Glu Tyr Asn Tyr Trp Gly Gln Gly Thr Gln Val Thr Val Ser Ser
            115                 120                 125
```

<210> SEQ ID NO 4
<211> LENGTH: 123
<212> TYPE: PRT
<213> ORGANISM: Camelus dromedarius

<400> SEQUENCE: 4

```
Gln Val Gln Leu Gln Glu Ser Gly Gly Gly Ser Val Gln Thr Gly Gly
1               5                   10                  15
Ser Leu Arg Leu Ser Cys Ala Ala Ser Gly Tyr Thr Phe Ser Ser Tyr
            20                  25                  30
Cys Met Gly Trp Phe Arg Gln Ala Pro Gly Lys Glu Arg Glu Leu Val
            35                  40                  45
Ser Thr Ile Ile Ser Asp Gly Ser Thr Tyr Tyr Ala Asp Ser Val Lys
        50                  55                  60
Gly Arg Phe Thr Ile Ser Gln Asp Asn Ala Lys Asn Thr Val Tyr Leu
65                  70                  75                  80
Gln Met Asn Asn Leu Lys Ala Glu Asp Thr Ala Ile Tyr Tyr Cys Ala
                85                  90                  95
Ala Arg Ser Gly Gly Val Cys Ser Gly Arg Ala Ser Arg Tyr Asn Tyr
               100                 105                 110
Trp Gly Gln Gly Thr Gln Val Thr Val Ser Ser
            115                 120
```

<210> SEQ ID NO 5
<211> LENGTH: 127
<212> TYPE: PRT

<213> ORGANISM: Camelus dromedarius

<400> SEQUENCE: 5

Gln Val Gln Leu Gln Glu Ser Gly Gly Gly Ser Val Gln Ala Gly Gly
1               5                   10                  15

Ser Leu Arg Leu Ser Cys Ala Ala Ser Gly Leu Pro Tyr Arg Thr Val
            20                  25                  30

Phe Met Gly Trp Phe Arg Gln Gly Pro Gly Lys Glu Arg Glu Gly Val
        35                  40                  45

Ala Val Ile Asn Ala Asp Gly Val Ser Thr Tyr Tyr Ala Asp Ser Val
    50                  55                  60

Lys Gly Arg Phe Thr Ile Ser Arg Asp Asn Ala Lys Asp Thr Val Tyr
65                  70                  75                  80

Leu Gln Met Asn Ser Leu Lys Pro Glu Asp Thr Ala Ile Tyr His Cys
                85                  90                  95

Ala Ala Asn His Phe Phe Asp Tyr Ser Arg Asp Pro Leu Ala Thr Ala
            100                 105                 110

Glu Tyr Asn Tyr Trp Gly Gln Gly Thr Gln Val Thr Val Ser Ser
        115                 120                 125

<210> SEQ ID NO 6
<211> LENGTH: 127
<212> TYPE: PRT
<213> ORGANISM: Camelus dromedarius

<400> SEQUENCE: 6

Gln Val Gln Leu Gln Glu Ser Gly Gly Gly Ser Val Gln Ala Gly Gly
1               5                   10                  15

Ser Leu Arg Leu Ser Cys Ala Ala Ser Gly Leu Pro Tyr Arg Thr Val
            20                  25                  30

Phe Met Gly Trp Phe Arg Gln Gly Pro Gly Lys Glu Arg Glu Gly Val
        35                  40                  45

Ala Val Ile Asn Ala Asp Gly Val Ser Thr Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Ile Tyr His Cys
                85                  90                  95

Ala Ala Asn His Phe Phe Asp Tyr Ser Arg Asp Pro Leu Ala Thr Ala
            100                 105                 110

Glu Tyr Asn Tyr Trp Gly Gln Gly Thr Gln Val Thr Val Ser Ser
        115                 120                 125

<210> SEQ ID NO 7
<211> LENGTH: 127
<212> TYPE: PRT
<213> ORGANISM: Camelus dromedarius

<400> SEQUENCE: 7

Gln Val Gln Leu Gln Glu Ser Gly Gly Gly Ser Val Gln Ala Gly Gly
1               5                   10                  15

Ser Leu Arg Leu Ser Cys Ala Ala Pro Gly Leu Pro Tyr Arg Val Val
            20                  25                  30

Phe Met Gly Trp Phe Arg Gln Gly Pro Gly Lys Glu Arg Glu Gly Val
        35                  40                  45

Ala Val Ile Asn Ala Asp Gly Val Ser Thr Tyr Tyr Ala Asp Ser Val
    50                  55                  60

```
Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Ile Tyr Tyr Cys
                 85                  90                  95

Ala Ala Asn His Phe Asp Tyr Ser Arg Asp Pro Leu Ala Thr Ala
            100                 105                 110

Glu Tyr Asn Tyr Trp Gly Gln Gly Thr Gln Val Thr Val Ser Ser
        115                 120                 125

<210> SEQ ID NO 8
<211> LENGTH: 130
<212> TYPE: PRT
<213> ORGANISM: Camelus dromedarius

<400> SEQUENCE: 8

Gln Val Gln Leu Gln Glu Ser Gly Gly Gly Ser Val Gln Ala Gly Gly
 1               5                  10                  15

Ser Leu Arg Leu Ala Cys Val Ala Ser Gly Gly Asp Thr Arg Pro Tyr
             20                  25                  30

Ile Thr Tyr Trp Met Gly Trp Tyr Arg Gln Ala Pro Gly Lys Glu Arg
         35                  40                  45

Glu Gly Val Ala Thr Ile Tyr Thr Gly Gly Ser Gly Thr Tyr Tyr Ser
 50                  55                  60

Asp Ser Val Glu Gly Arg Phe Thr Ile Ser Gln Asp Lys Ala Gln Arg
 65                  70                  75                  80

Thr Val Tyr Leu Gln Met Asn Asp Leu Lys Pro Glu Asp Thr Gly Met
                 85                  90                  95

Tyr Tyr Cys Ala Ala Gly Asn Gly Ala Leu Pro Pro Gly Arg Arg Leu
            100                 105                 110

Ser Pro Gln Asn Met Asp Thr Trp Gly Pro Gly Thr Gln Val Thr Val
        115                 120                 125

Ser Ser
    130

<210> SEQ ID NO 9
<211> LENGTH: 117
<212> TYPE: PRT
<213> ORGANISM: Vicugna pacos

<400> SEQUENCE: 9

Gln Val Gln Leu Gln Glu Ser Gly Gly Gly Leu Val Gln Pro Gly Gly
 1               5                  10                  15

Ser Leu Arg Leu Ser Cys Arg Ala Ser Glu Ser Leu Phe Ser Leu Tyr
             20                  25                  30

Ala Met Gly Trp Tyr Arg Gln Ala Pro Gly Lys Gln Pro Glu Leu Ile
         35                  40                  45

Ala Thr Ile Ser Gly Gly Gly Glu Gly Thr Gly Asn Tyr Ala Asp Pro
 50                  55                  60

Val Lys Gly Arg Phe Thr Ile Ser Arg Asn Asn Ala Asn Asn Met Val
 65                  70                  75                  80

Phe Leu Gln Met Asn Ser Leu Lys Pro Glu Asp Thr Ala Val Tyr Tyr
                 85                  90                  95

Cys Asn Val Tyr Gly Thr Asn Leu Ala Pro Trp Gly Gln Gly Thr Gln
            100                 105                 110

Val Thr Val Ser Ser
        115
```

<210> SEQ ID NO 10
<211> LENGTH: 117
<212> TYPE: PRT
<213> ORGANISM: Vicugna pacos

<400> SEQUENCE: 10

Gln Val Gln Leu Gln Glu Ser Gly Gly Gly Leu Val Gln Pro Gly Gly
1               5                   10                  15

Ser Leu Arg Leu Ser Cys Arg Ala Ser Glu Thr Leu Phe Ser Leu Tyr
            20                  25                  30

Ala Met Gly Trp Tyr Arg Gln Ala Pro Gly Lys Gln Pro Glu Leu Ile
        35                  40                  45

Ala Thr Ile Ser Gly Gly Gly Glu Gly Thr Gly Asn Tyr Ala Asp Pro
    50                  55                  60

Val Lys Gly Arg Phe Thr Ile Ser Arg Asn Asn Ala Asn Asn Met Val
65                  70                  75                  80

Phe Leu Gln Met Asn Asn Leu Lys Pro Glu Asp Thr Ala Val Tyr Tyr
                85                  90                  95

Cys Asn Val Tyr Gly Thr Asn Leu Ala Pro Trp Gly Gln Gly Thr Gln
            100                 105                 110

Val Thr Val Ser Ser
        115

<210> SEQ ID NO 11
<211> LENGTH: 117
<212> TYPE: PRT
<213> ORGANISM: Vicugna pacos

<400> SEQUENCE: 11

Gln Val Gln Leu Gln Glu Ser Gly Gly Gly Leu Val Gln Pro Gly Gly
1               5                   10                  15

Ser Leu Arg Leu Ser Cys Arg Val Ser Glu Ser Leu Phe Ser Leu Tyr
            20                  25                  30

Ala Met Gly Trp Tyr Arg Gln Ala Pro Gly Lys Gln Pro Glu Leu Ile
        35                  40                  45

Ala Thr Ile Ser Gly Gly Gly Glu Gly Thr Gly Asn Tyr Ala Asp Pro
    50                  55                  60

Val Lys Gly Arg Phe Thr Ile Ser Arg Asn Asn Ala Asn Asn Thr Val
65                  70                  75                  80

Phe Leu Gln Met Asn Ser Leu Lys Pro Glu Asp Thr Ala Val Tyr Tyr
                85                  90                  95

Cys Asn Val Tyr Gly Thr Asn Leu Ala Pro Trp Gly Gln Gly Thr Gln
            100                 105                 110

Val Thr Val Ser Ser
        115

<210> SEQ ID NO 12
<211> LENGTH: 117
<212> TYPE: PRT
<213> ORGANISM: Vicugna pacos

<400> SEQUENCE: 12

Gln Val Gln Leu Gln Glu Ser Gly Gly Gly Leu Val Gln Pro Gly Gly
1               5                   10                  15

Ser Leu Arg Leu Ser Cys Arg Ala Ser Glu Ser Leu Phe Ser Leu Tyr
            20                  25                  30

```
Ala Met Gly Trp Tyr Arg Gln Ala Pro Gly Lys Gln Pro Glu Leu Ile
            35                  40                  45

Ala Thr Ile Ser Gly Gly Glu Gly Thr Gly Asn Tyr Ala Asp Pro
 50                  55                  60

Val Lys Gly Arg Phe Thr Ile Ser Arg Asn Asn Ala Asn Asn Thr Val
 65                  70                  75                  80

Phe Leu Gln Met Asn Ser Leu Lys Pro Glu Asp Thr Ala Val Tyr Tyr
                 85                  90                  95

Cys Asn Val Tyr Gly Thr Asn Leu Ala Pro Trp Gly Gln Gly Thr Gln
                100                 105                 110

Val Thr Val Ser Ser
        115

<210> SEQ ID NO 13
<211> LENGTH: 117
<212> TYPE: PRT
<213> ORGANISM: Vicugna pacos

<400> SEQUENCE: 13

Gln Val Gln Leu Gln Glu Ser Gly Gly Gly Leu Val Gln Pro Gly Gly
 1               5                  10                  15

Ser Leu Arg Leu Ser Cys Ala Ala Ser Glu Thr Leu Phe Ser Leu Tyr
            20                  25                  30

Ala Met Gly Trp Tyr Arg Gln Ala Pro Gly Lys Gln Pro Glu Leu Ile
            35                  40                  45

Ala Thr Ile Ser Gly Gly Glu Gly Thr Gly Asn Tyr Ala Asp Pro
 50                  55                  60

Val Lys Gly Arg Phe Thr Ile Ser Arg Asn Asn Ala Asp Asn Met Val
 65                  70                  75                  80

Phe Leu Gln Met Asn Asn Leu Lys Pro Glu Asp Thr Ala Val Tyr Tyr
                 85                  90                  95

Cys Asn Val Tyr Gly Thr Asn Leu Ala Pro Trp Gly Gln Gly Thr Gln
                100                 105                 110

Val Thr Val Ser Ser
        115

<210> SEQ ID NO 14
<211> LENGTH: 117
<212> TYPE: PRT
<213> ORGANISM: Vicugna pacos

<400> SEQUENCE: 14

Gln Val Gln Leu Gln Glu Ser Gly Gly Gly Leu Val His Ser Gly Gly
 1               5                  10                  15

Ser Leu Arg Leu Ser Cys Arg Val Ser Glu Ser Leu Phe Ser Leu Tyr
            20                  25                  30

Ala Met Gly Trp Tyr Arg Gln Ala Leu Gly Lys Gln Pro Glu Leu Ile
            35                  40                  45

Ala Thr Ile Ser Gly Gly Gly Glu Gly Thr Gly Asn Tyr Ala Asp Pro
 50                  55                  60

Val Lys Gly Arg Phe Thr Ile Ser Arg Asn Asn Ala Asn Asn Thr Val
 65                  70                  75                  80

Phe Leu Gln Met Asn Ser Leu Lys Pro Glu Asp Thr Ala Val Tyr Tyr
                 85                  90                  95

Cys Asn Val Tyr Gly Thr Asn Leu Ala Pro Trp Gly Gln Gly Thr Gln
                100                 105                 110
```

```
Val Thr Val Ser Ser
        115

<210> SEQ ID NO 15
<211> LENGTH: 13
<212> TYPE: PRT
<213> ORGANISM: Camelus dromedarius

<400> SEQUENCE: 15

Gly Gly Asp Thr Arg Pro Tyr Ile Thr Tyr Trp Met Gly
1               5                   10

<210> SEQ ID NO 16
<211> LENGTH: 17
<212> TYPE: PRT
<213> ORGANISM: Camelus dromedarius

<400> SEQUENCE: 16

Thr Ile Tyr Thr Gly Gly Ser Gly Thr Tyr Tyr Ser Asp Ser Val Glu
1               5                   10                  15

Gly

<210> SEQ ID NO 17
<211> LENGTH: 18
<212> TYPE: PRT
<213> ORGANISM: Camelus dromedarius

<400> SEQUENCE: 17

Gly Asn Gly Ala Leu Pro Pro Gly Arg Arg Leu Ser Pro Gln Asn Met
1               5                   10                  15

Asp Thr

<210> SEQ ID NO 18
<211> LENGTH: 10
<212> TYPE: PRT
<213> ORGANISM: Vicugna pacos

<400> SEQUENCE: 18

Glu Thr Leu Phe Ser Leu Tyr Ala Met Gly
1               5                   10

<210> SEQ ID NO 19
<211> LENGTH: 10
<212> TYPE: PRT
<213> ORGANISM: Vicugna pacos

<400> SEQUENCE: 19

Glu Ser Leu Phe Ser Leu Tyr Ala Met Gly
1               5                   10

<210> SEQ ID NO 20
<211> LENGTH: 18
<212> TYPE: PRT
<213> ORGANISM: Vicugna pacos

<400> SEQUENCE: 20

Thr Ile Ser Gly Gly Gly Glu Gly Thr Gly Asn Tyr Ala Asp Pro Val
1               5                   10                  15

Lys Gly

<210> SEQ ID NO 21
<211> LENGTH: 7
<212> TYPE: PRT
```

<213> ORGANISM: Vicugna pacos

<400> SEQUENCE: 21

Tyr Gly Thr Asn Leu Ala Pro
1               5

<210> SEQ ID NO 22
<211> LENGTH: 10
<212> TYPE: PRT
<213> ORGANISM: Camelus dromedarius

<400> SEQUENCE: 22

Gly Leu Pro Tyr Arg Thr Val Phe Met Gly
1               5                   10

<210> SEQ ID NO 23
<211> LENGTH: 10
<212> TYPE: PRT
<213> ORGANISM: Camelus dromedarius

<400> SEQUENCE: 23

Gly Leu Pro Tyr Arg Val Val Phe Met Gly
1               5                   10

<210> SEQ ID NO 24
<211> LENGTH: 17
<212> TYPE: PRT
<213> ORGANISM: Camelus dromedarius

<400> SEQUENCE: 24

Val Ile Asn Ala Asp Gly Val Ser Thr Tyr Tyr Ala Asp Ser Val Lys
1               5                   10                  15

Gly

<210> SEQ ID NO 25
<211> LENGTH: 18
<212> TYPE: PRT
<213> ORGANISM: Camelus dromedarius

<400> SEQUENCE: 25

Asn His Phe Phe Asp Tyr Ser Arg Asp Pro Leu Ala Thr Ala Glu Tyr
1               5                   10                  15

Asn Tyr

<210> SEQ ID NO 26
<211> LENGTH: 10
<212> TYPE: PRT
<213> ORGANISM: Camelus dromedarius

<400> SEQUENCE: 26

Gly Tyr Thr Phe Ser Ser Tyr Cys Met Gly
1               5                   10

<210> SEQ ID NO 27
<211> LENGTH: 16
<212> TYPE: PRT
<213> ORGANISM: Camelus dromedarius

<400> SEQUENCE: 27

Thr Ile Ile Ser Asp Gly Ser Thr Tyr Tyr Ala Asp Ser Val Lys Gly
1               5                   10                  15

<210> SEQ ID NO 28

```
<211> LENGTH: 15
<212> TYPE: PRT
<213> ORGANISM: Camelus dromedarius

<400> SEQUENCE: 28

Arg Ser Gly Gly Val Cys Ser Gly Arg Ala Ser Arg Tyr Asn Tyr
1               5                   10                  15
```

SINGLE DOMAIN ANTIBODIES AGAINST SOD1 AND THEIR USE IN MEDICINE

CROSS-REFERENCE TO RELATED APPLICATIONS

This application is a national phase entry under 35 U.S.C. §371 of International Patent Application PCT/EP2014/061129, filed May 28, 2014, designating the United States of America and published in English as International Patent Publication WO 2014/191493 A1 on Dec. 4, 2014, which claims the benefit under Article 8 of the Patent Cooperation Treaty and under 35 U.S.C. §119(e) to European Patent Application Serial No. 13169476.2, filed May 28, 2013.

STATEMENT ACCORDING TO 37 C.F.R. §1.821(C) OR (E)—SEQUENCE LISTING SUBMITTED AS PDF FILE WITH A REQUEST TO TRANSFER CRF FROM PARENT APPLICATION

Pursuant to 37 C.F.R. §1.821(c) or (e), a file containing a PDF version of the Sequence Listing has been submitted concomitant with this application, the contents of which are hereby incorporated by reference. The transmittal documents of this application include a Request to Transfer CRF from the parent application.

TECHNICAL FIELD

This disclosure relates to the field of single-domain antibodies (also called nanobodies), more particularly, single-domain antibodies against SOD1 protein isoforms. It also relates to the use of these nanobodies in medicine. Accordingly, methods to treat a disease using these nanobodies are provided herein. The single-domain antibodies are particularly envisaged for treatment of ALS.

BACKGROUND

There currently is no effective treatment for neurodegenerative diseases such as Alzheimer's disease, Parkinson's disease, Huntington's disease, and amyotrophic lateral sclerosis (ALS). In all of these disorders, proteins in which mutations induce a toxic gain of function are thought to play a causal or pathogenic role. This newly acquired toxic function often is either multifactorial or incompletely understood. Reducing the expression of the mutant protein is one therapeutic strategy of which the success is independent of the understanding of the pathogenic action of the protein.

ALS is an adult-onset neurodegenerative disease that affects the upper and lower motoneurons (MNs) in the cerebral cortex, brain stem, and spinal cord. It results in progressive MN loss, muscle paralysis and atrophy leading to death within a few years. Most ALS patients are thought to have a sporadic form of the disease, but in about 10% of patients, ALS is inherited or familial (FALS). In about 20% of patients with FALS, the disease is caused by mutations in the gene encoding Cu/Zn-superoxide dismutase (SOD1) (Rosen et al., 1993). Other causes are mutations in TARP, FUS/TLS, VCP and C9ORF72. Overexpression of mutated human SOD1 in transgenic animals, both mice (Gurney et al., 1994) and rats (Nagai et al., 2001), results in the development of a lethal motor neuron disease. More than 150 distinct SOD1 point mutations have been described including cases in which enzymatic activity is increased, decreased or non-altered (cf. the ALS Online genetics Database on the World Wide Web at alsod.iop.kcl.ac.uk/). Therefore, a toxic gain of function is generally accepted to underlie neuronal toxicity of mutant SOD1. Mutant SOD1 has been found to be misfolded,[4-5] and it is hypothesized that this toxicity is related to the formation of high-molecular-weight complexes and, in a final stage, the formation of aggregates,[6-7] a hallmark of many neurodegenerative diseases (Zhang and Zhu, 2006; Ross and Poirier, 2004).

Furthermore, wild-type SOD1 has been suggested to play a role in the pathogenesis of sporadic ALS.[8] It has been proposed that in sporadic ALS, wild-type SOD1 undergoes secondary modifications (e.g., through oxidation or demetalation), misfolds and is toxic to motor neurons in a very similar manner to what is seen with mutant SOD1.[9] Using a conformation-specific antibody that recognizes the misfolded species selectively, pathogenic SOD1 has been found in motor neurons of at least a part of sporadic ALS patients.[1] Most interestingly, the toxic effect of astrocytes from sporadic ALS patients (thus not harboring SOD1 mutations) on motor neurons is dependent on the presence of SOD1.[2]

Therefore, reducing the levels of the pathogenic SOD1 is an interesting strategy to treat patients with mutant SOD1-associated familial ALS, as well as patients with sporadic ALS. To achieve this, anti-sense oligonucleotide, siRNA-based and immunological approaches have been developed. For the latter, both active and passive immunization is under investigation. However, approaches using siRNA and conventional antibodies come with significant problems (e.g., half-life, distribution in the CNS, uptake by neurons, etc.), and none of these approaches has thus far led to a therapy for ALS.

Accordingly, there is a pressing need for new therapies for ALS, particularly therapies that address the above-mentioned problems.

BRIEF SUMMARY

Many neurodegenerative diseases such as Alzheimer's and Parkinson's disease, Huntington's disease and amyotrophic lateral sclerosis (ALS) are caused by a mutant protein that, through the presence of this mutation, gains a function that is toxic for the cell. Reducing the levels of the pathogenic mutant protein would be one strategy to treat patients suffering from these disorders.

To avoid all problems inherent with the use of conventional antibodies, it was explored as to whether nanobodies can be used in the treatment of neurodegenerative disease and, in particular, of ALS.

In 1993, Hamers-Castermans et al.[14] described that camelids and some sharks produce functional antibodies devoid of light chains of which the single variable N-terminal domain was fully capable of antigen binding. This so-called VHH domain can be cloned and the product, called nanobody or single-domain antibody, shows high target specificity and affinity, and low inherent toxicity.[15-17] Furthermore, nanobodies are highly soluble, extremely stable, have refolding capacity, can be administered by means other than injection, and are relatively easy to manufacture.[18]

Nanobodies have a potential use as therapeutics in many fields.[3,4] Nanobodies have, like conventional forms of antibodies, applications as diagnostic markers.[5,6] Furthermore, nanobodies can be used as structural probes of protein misfolding and fibril formation.[7] Nanobodies that are capable of influencing the aggregation pathway of a disease-related protein, either by inhibiting the formation of particular intermediates or by neutralizing their neurotoxic effects, could also serve as potential therapeutics.

Nanobodies have additional properties that make them particularly appealing as therapeutic and diagnostic agents, including low immunogenicity due to high sequence similarities with human VH family III.[8] Particularly important for their potential use in neurodegenerative disorders, they have been shown to be able, in at least some cases, to cross the blood-brain barrier efficiently.[9] Nanobodies against α-synuclein,[10, 11] β-amyloid,[12, 13] and huntingtin[14] have been already raised, and it has been reported to inhibit α-synuclein, β-amyloid and huntingtin aggregation in in vitro models for Parkinson's, Alzheimer's and Huntington's disease.

ALS is an adult-onset fatal neurodegenerative disease that is familial in about 10% of patients. In about 20% of patients with familial ALS (FALS), the disease is caused by gain-of-toxic-function mutations in the gene encoding Cu/Zn-superoxide dismutase (SOD1). To reduce the expression of mutant SOD1 in the motor neurons, anti-SOD1 heavy chain antibodies were raised in dromedaries and alpacas, and cloned their N-terminal antigen-binding VHH region, coding for anti-SOD1 nanobodies.

The therapeutic potential of such nanobodies was investigated in ALS by studying their effect on mutant SOD1-induced toxicity in vitro and in vivo and testing it in different ALS models. Different approaches were used: transfection or injection of constructs that express an SOD1 nanobody and also the administration of SOD1 nanobody itself. It could be shown that SOD1 nanobodies have high affinity for SOD1 in vitro and dose-dependently block its fibril formation, their expression reduces mutant SOD1 levels and rescues mutant SOD1-induced axonopathy in zebrafish and inhibits SOD1 aggregates formation in in vitro models for ALS. In vivo, SOD1 nanobody also rescues mutant SOD1-induced axonopathy in zebrafish when added in the tank water. Moreover, administering a nanobody to symptomatic hSOD1$^{G93A}$ mice, a murine model for ALS, extends their lifespan in a dose-dependent way. These data demonstrate the potential use of SOD1 nanobodies as a novel therapeutic strategy for ALS. Moreover, they might be broadly applicable for neurodegenerative disease in general caused by toxicity of a mutant protein.

Thus, provided are single-domain antibodies (or nanobodies) against SOD1. According to particular embodiments, SOD1 is human SOD1. According to alternative, but not exclusive, embodiments, the single-domain antibodies bind to mutant SOD1, i.e., they recognize an epitope that is present in a mutated form of the SOD1 protein. According to further particular embodiments, the mutant SOD1 is characterized by a mutation of amino acids at positions 4, 93 and/or 113, particularly by an A4V, G93A, and/or G113W mutation. According to yet further embodiments, the single domain antibodies bind both wild-type and mutant SOD1 (i.e., they recognize an epitope present in the wild-type protein and at least one (but possibly more) mutated isoform).

According to particular embodiments, the single-domain antibody is an inhibitory single-domain antibody against SOD1. Typically, this means that the nanobody interferes with the superoxide dismutase function of SOD1. However, according to particular embodiments, the inhibitory single-domain antibody inhibits the toxic gain of function of mutant SOD1 protein. Most particularly, the single-domain antibody interferes with (inhibits, prevents, reverses or slows) the formation of SOD1 aggregates; and/or the single-domain antibody can counter the phenotypic changes caused by expression of the mutant SOD1 protein (e.g., axonopathy).

According to particular embodiments, the single-domain antibody has a sequence selected from the group of SEQ ID NOS:1-14. According to alternative embodiments, the single-domain antibody shares the sequence of the complementarity-determining regions of these sequences.

The single-domain antibody may be provided as such or may be fused to further moieties. According to particular embodiments, the single-domain antibody is fused to a tag. According to further particular embodiments, the tag to which the single-domain antibody is fused is a His-tag, HA-tag, and/or Myc-tag.

SOD1 normally is a soluble cytoplasmic protein, although a detrimental or neurotoxic role has been ascribed, both to extracellular secreted SOD1 and cytoplasmic mutant SOD1. In order to be able to inhibit intracellular forms of SOD1, according to particular embodiments, the nanobody is able to enter cells, particularly neuronal cells. This may be an inherent property of the nanobody, or may be achieved by further fusion to moieties or tags that allow cellular uptake.

According to particular embodiments, the single-domain antibodies are not provided as such, but are provided as nucleic acid molecules, i.e., nucleic acid molecules encoding single-domain antibodies against SOD1 as herein described. Also provided are vectors comprising such nucleic acids or nucleic acid molecules. According to yet further embodiments, host cells are provided comprising such nucleic acids or such vectors.

According to a further aspect, the single-domain antibodies are provided herein for use in medicine. That is to say, the single-domain antibodies against SOD1 are provided for use as a medicament. The same goes for the nucleic acid molecules encoding the single-domain antibodies, or for the vectors containing such nucleic acids. According to particular embodiments, the single-domain antibodies (or nucleic acids encoding them, or vectors comprising such nucleic acids) are provided for use in treatment of amyotrophic lateral sclerosis (ALS).

This is equivalent as saying that methods are provided for treating ALS, or of improving symptoms of ALS in a subject in need thereof, comprising administering a single-domain antibody against SOD1 to the subject. Here also, the single-domain antibody may be provided as protein, or may be administered as a nucleic acid molecule encoding a single-domain antibody against SOD1, or as a vector comprising such nucleic acid molecule. If the single-domain antibody is administered as protein, it is particularly envisaged that it is administered intracerebroventricularly, such as, e.g., through injection or pump.

In the case where the single-domain antibody is provided as a nucleic acid or a vector, it is particularly envisaged that the single-domain antibody is administered through gene therapy.

According to particular embodiments, the methods further comprise a step of monitoring the progression of ALS (or ALS symptoms) in the subject.

According to further embodiments, kits are provided comprising a single-domain antibody against SOD1 and a pharmaceutically acceptable excipient. According to particular embodiments, the single-domain antibody may be provided as a protein, as a nucleic acid encoding a single-domain antibody against SOD1, or as a vector comprising such nucleic acid.

BRIEF DESCRIPTION OF THE DRAWINGS

FIG. 1A, Western Dot Blot showing the binding of nanobodies to immobilized recombinant SOD1. FIG. 1B, characterization of the binding properties of the nanobodies. FIG. 1C, the SOD1 Nb1 and Nb2 block fibril formation in vitro. FIG. 1D, TEM pictures showing that Nb1 prevents aggregate formation in samples containing both Nb1 and SOD1.

FIGS. 2A-2C: SOD1 nanobodies reduce SOD1 aggregation in HeLa cells. FIG. 2A, expression of HA-tag Nb and SOD1-CFP in HeLa cells. FIG. 2B, Nb expressed in mammalian cells retain binding capacity for SOD1 as shown after co-purifying together SOD1 Nb and SOD1. FIG. 2C, analysis of the nanobodies in transiently transfected HeLa cells by Blue Native Polyacrylamide gel electrophoresis (BN-PAGE).

FIGS. 5A-5C: SOD1 nanobody expressed in NSC34 cells recognizes SOD1 protein and does not decrease hSOD1 levels. After SOD1 and nanobody co-transfection, SOD1 nanobody (FIG. 5A) but not control nanobody (FIG. 5B) can recognize and bind to endogenous, WT and mutant SOD1 (both G93A and A4V). However, SOD1 nanobody does not reduce hSOD1 levels after co-transfection (FIG. 5C).

FIG. 6A, injected SOD1 nanobody in zebrafish can also be detected through the HA-tag. FIG. 6B, expression levels of SOD1 decrease with the co-injection of SOD1 nanobody and SOD1$^{A4V}$, but not when co-injected with control nanobody. FIG. 6C, shortening of motor neuron axons is partially rescued with the co-injection of SOD1$^{A4V}$ with SOD1 nanobody but not with the control nanobody.

FIG. 7A, the SOD1 nanobody can be detected through its His-tag by Western blot and when it is added to the NSC-34 culture medium (FIG. 7B) can be found associated with the cells. Co-localization of the mutant SOD1 and the SOD1 nanobody (but not the control nanobody) was found by fluorescence (FIG. 7C) and confocal microscopy (FIG. 7D).

FIGS. 8A-8D: The SOD1 nanobody can enter the cell through its His-tag and reduce the number of cells with mSOD1 aggregates. After cell fractionation, SOD1 nanobody can be found in the cytosol (FIG. 8A) and after immunoprecipitation, it has been found to bind SOD1 (FIG. 8B). 48 hours after administration in the cell medium, the SOD1 nanobody inhibits aggregate formation in a dose-dependent manner (FIG. 8C). The inhibition is blocked when the His-tag is removed from the nanobody (FIG. 8D).

FIGS. 11A-11E: SOD1 nanobody can be detected in the mouse CNS after injection and binds SOD1. FIG. 11A, map of the mouse brain and scheme of the ICV injection. After one single injection, the SOD1 nanobody can be found in different areas of the brain (FIG. 11B) and spinal cord (FIG. 11C). FIG. 11D, the SOD1 nanobody is clear 12 hours after injection and weakly detected after 24 hours. The SOD1 nanobody, through its His-tag, can be immunoprecipitated with SOD1 in injected hSOD1$^{G93A}$ mice (FIG. 11E).

FIGS. 12A-12D: The survival and disease onset are increased in treated hSOD1$^{G93A}$ mice. Survival (FIG. 12A) and disease onset (FIG. 12D) of hSOD1$^{G93A}$ mice treated with the SOD1 nanobody are delayed when the treatment is administrated starting at P60, at P90 (FIG. 12B) and P120 (FIG. 12C), 3 times/week. With daily injections starting at P90, the survival is also significantly increased.

FIGS. 13A and 13B: The SOD1 nanobody rescues MN death. The number of small MN, but not of big MN, was increased at P145 in mice treated with SOD1 nanobody from P60 (FIG. 13A). The number of MNJ did not vary (FIG. 13B).

FIG. 14: The SOD1 nanobody recognizes neurotoxic forms of SOD1. In injected hSOD1$^{G93A}$ mice, the SOD1 nanobody, through its His-tag, can be immunoprecipitated with the antibody anti-P2X$_4$, that selectively recognizes special conformers of mutant SOD1 that are neurotoxic.

FIG. 15: Amino acid sequences of 14 different nanobodies specific for human SOD1 (superoxide dismutase) (Cu—Zn). All Nanobodies originate from VHH germline sequences. The complementarity-determining regions (CDRs) are shown in bold. The top seven nanobodies were isolated from an immune library from a dromedary. The bottom seven nanobodies were isolated from an immune library from an alpaca. The above 14 different nanobodies represent four different groups shown in four different colors. Nanobodies belonging to the same group (with the same color) are very similar and their amino acid sequences suggest that they are from clonally related B-cells resulting from somatic hyper-mutation or from the same B-cell but diversified due to PCR error during library construction. The gaps were introduced in order to align sequences.

DETAILED DESCRIPTION

Definitions

Figure 1A:
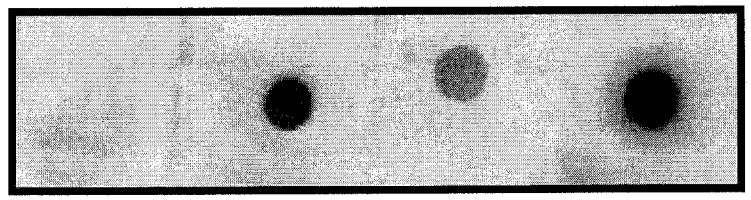
FIGS. 1A-1D: SOD1 nanobodies have high affinity for SOD1 in vitro and block its fibril formation.

This disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual*, 2$^{nd}$ ed., Cold Spring Harbor Press, Plainsview, N.Y. (1989); and Ausubel et al., *Current Protocols in Molecular Biology* (Supplement 47), John Wiley & Sons, New York (1999), for definitions and terms of the art. The definitions provided herein should not be construed to have a scope less than understood by a person of ordinary skill in the art.

A "single-domain antibody" (sdAb), also referred to as "nanobody" herein, is an antibody fragment consisting of a single monomeric variable antibody domain. Like a whole antibody, it is able to bind selectively to a specific antigen. With a molecular weight of only 12 to 15 kDa, single-domain antibodies are much smaller than common antibodies (150 to 160 kDa), which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

The term "SOD1" as used herein refers to the gene superoxide dismutase 1 and its encoded protein (Gene ID: 6647 for the human gene). The enzyme SOD1 binds copper and zinc ions and is one of three superoxide dismutases responsible for destroying free superoxide radicals in the body. Mutations in this gene have been linked to familial amyotrophic lateral sclerosis, and several pieces of evidence also show that wild-type SOD1, under conditions of cellular stress, is implicated in a significant fraction of sporadic ALS cases. Over 150 mutations of SOD1 have been linked to ALS (cf. the ALS online genetics database on the World Wide Web at alsod.iop.kcl.ac.uk/; see also Olubunmi Abel, John F. Powell, Peter M. Andersen, Ammar Al-Chalabi "ALSoD: A user-friendly online bioinformatics tool for amyotrophic lateral sclerosis genetics," *Hum. Mutat.* 2012); "mutant SOD1," in particular, refers to SOD1 containing one or more mutations that are linked to ALS. Selected examples (listed as one-letter amino acid abbreviations, with numbering referring to the human protein) include those listed in the OMIM database under entry 147450, i.e., SOD1 A4V, G93A, G113W, H46R, G37R, L38V, G41D, H43R, G85R, G93C, G93A, E100G, L106V, I113T, A4T, D90A, I104F, L144S, A145T; IVS4AS, T-G, -10; C6F, T151I, E21K, S134N, L84V, G16S, L126X; IVS4AS, A-G, -11; G72S, G12R, F45C, H80A, D96N; 6-BP DEL, GGACCA; and IVS4AS, C-G, and -304.

The term "inhibitory" as used in the phrase "inhibitory single-domain antibody" or "inhibitory nanobody" herein, refers to the fact that the nanobody can inhibit the function and/or activity of its target protein. In case of wild-type SOD1, this means that the superoxide dismutase activity is inhibited. In case of mutant SOD1 that has a gain of function, typically it is meant that the (toxic) new function is inhibited, although this may also mean that the enzymatic activity is inhibited, or inhibited as well. For instance, inhibition may result in decrease of aggregation of mutant SOD1. Importantly, inhibition or decrease in toxic function may also be evaluated as an increase of another parameter, e.g., the inhibition may be evaluated by an increase in axonal length or an extended life span. "Inhibitory" can mean full inhibition (no enzymatic activity and/or toxic effect is observable) or may mean partial inhibition. For instance, inhibition can mean 10% inhibition, 20% inhibition, 25% inhibition, 30% inhibition, 40% inhibition, or more. Particularly, inhibition will be at least 50%, e.g., 50% inhibition, 60% inhibition, 70% inhibition, 75% inhibition, 80% inhibition, 90% inhibition, 95% inhibition or more. Percentage of inhibition typically will be evaluated against a suitable control (e.g., treatment with an irrelevant nanobody, or a wild-type subject versus a diseased subject), as will be readily chosen by the skilled person.

The term "ALS" or "amyotrophic lateral sclerosis" as used herein, sometimes also known as Lou Gehrig's disease, is a neurodegenerative disorder characterized by the death of motor neurons in the brain, brainstem, and spinal cord, resulting in fatal paralysis. It is a genetically heterogeneous disorder, described under entry 105400 in the OMIM database. A particular subset of ALS is ALS with SOD1 involvement, either through mutated SOD1 (OMIM entry 147450) or in cases where wild-type SOD1 is involved (typically in conditions of cellular stress).

A "subject" as used herein refers to an animal that can develop ALS wherein SOD1 is involved (e.g., through misfolding). Typically, the animal is a mammal. Most particularly, the subject is a human.

Provided are single-domain antibodies (or nanobodies) against SOD1. According to particular embodiments, SOD1 is human SOD1. According to alternative, but not exclusive, embodiments, the single-domain antibodies bind to mutant SOD1, i.e., they recognize an epitope that is present in a mutated form of the SOD1 protein. According to further particular embodiments, the mutant SOD1 is characterized by a mutation of amino acids at positions 4, 93 and/or 113, particularly by an A4V, G93A, and/or G113W mutation. According to yet further embodiments, the single-domain antibodies bind both wild-type and mutant SOD1 (i.e., they recognize an epitope present in the wild-type protein and at least one (but possibly more) mutated isoform).

According to particular embodiments, the single-domain antibody is an inhibitory single-domain antibody against SOD1. Typically, this means that the nanobody interferes with the superoxide dismutase function of SOD1. However, according to particular embodiments, the inhibitory single-domain antibody inhibits the toxic gain of function of mutant SOD1 protein. Most particularly, the single-domain antibody interferes with (inhibits, prevents, reverses or slows) the formation of SOD1 aggregates; and/or the single-domain antibody can counter the phenotypic changes caused by expression of the mutant SOD1 protein (e.g., axonopathy).

According to particular embodiments, the single-domain antibody has a sequence selected from the group of SEQ ID NOS:1-14. According to alternative embodiments, the single-domain antibody shares the sequence of the complementarity-determining regions (CDRs) of these sequences, fitted in a suitable framework region. For Nb2 (SEQ ID NO:1) and related nanobodies, the three CDR sequences correspond to GGDTRPYITYWMG (SEQ ID NO:15), TIYTGGSGTYYSDSVEG (SEQ ID NO:16) and GNGALPPGRRLSPQNMDT (SEQ ID NO:17), respectively. For Nb1 and related nanobodies, the CDR sequences correspond to ETLFSLYAMG (SEQ ID NO:18) or ESLF- SLYAMG (SEQ ID NO:19), TISGGGEGTGNYADPVKG (SEQ ID NO:20) and YGTNLAP (SEQ ID NO:21), respectively. For Nb3 and related nanobodies, the CDR sequences correspond to GLPYRTVFMG (SEQ ID NO:22) or GLPYRVVFMG (SEQ ID NO:23), VINADGVSTYYADSVKG (SEQ ID NO:24), and NHFFDYSRDPLATAEYNY (SEQ ID NO:25), respectively. For Nb4, the sequences of the CDRs are GYTFSSYCMG (SEQ ID NO:26), TIISDGSTYYADSVKG (SEQ ID NO:27) and RSGGVCSGRASRYNY (SEQ ID NO:28), respectively.

The single-domain antibody may be provided as such or may be fused to further moieties. According to particular embodiments, the single-domain antibody is fused to a tag. According to further particular embodiments, the tag to which the single-domain antibody is fused is a His-tag, HA-tag, and/or Myc-tag.

SOD1 normally is a soluble cytoplasmic protein, although a detrimental or neurotoxic role has been ascribed both to extracellular secreted SOD1 and cytoplasmic mutant SOD1. In order to be able to inhibit intracellular forms of SOD1, according to particular embodiments, the nanobody is able to enter cells, particularly neuronal cells. This may be an inherent property of the nanobody, or may be achieved by further fusion to moieties or tags that allow cellular uptake.

According to particular embodiments, the single-domain antibodies are not provided as such, but are provided as nucleic acid molecules, i.e., nucleic acid molecules encoding single-domain antibodies against SOD1 as herein described. Also provided are vectors comprising such nucleic acids or nucleic acid molecules. According to yet further embodiments, host cells are provided comprising such nucleic acids or such vectors.

According to a further aspect, the single-domain antibodies are provided herein for use in medicine. That is to say, the single-domain antibodies against SOD1 are provided for use as a medicament. The same goes for the nucleic acid molecules encoding the single-domain antibodies, or for the vectors containing such nucleic acids. According to particular embodiments, the single-domain antibodies (or nucleic acids encoding them, or vectors comprising such nucleic acids) are provided for use in treatment of amyotrophic lateral sclerosis (ALS).

This is equivalent as saying that methods are provided for treating ALS, or of improving symptoms of ALS, in a subject in need thereof, comprising administering a single-domain antibody against SOD1 to the subject. Here also, the single-domain antibody may be provided as protein, or may be administered as a nucleic acid molecule encoding a single-domain antibody against SOD1, or as a vector comprising such nucleic acid molecule. If the single-domain antibody is administered as protein, it is particularly envisaged that it is administered intracerebroventricularly, such as, e.g., through injection or pump.

In case the single-domain antibody is provided as a nucleic acid or a vector, it is particularly envisaged that the single-domain antibody is administered through gene therapy.

According to particular embodiments, the methods further comprise a step of monitoring the progression of ALS (or ALS symptoms) in the subject.

According to further embodiments, kits are provided comprising a single-domain antibody against SOD1 and a pharmaceutically acceptable excipient. According to particular embodiments, the single-domain antibody may be provided as protein, as a nucleic acid encoding a single-domain antibody against SOD1, or as a vector comprising such nucleic acid.

It is to be understood that although particular embodiments, specific configurations, as well as materials and/or molecules, have been discussed herein for cells and methods according to this disclosure, various changes or modifications in form and detail may be made without departing from the scope and spirit of this disclosure. The following examples are provided to better illustrate particular embodiments, and they should not be considered limiting the disclosure; the disclosure is limited only by the claims.

EXAMPLES

Materials and Methods

Generation of SOD1 Nanobodies

Nanobodies were generated as described before.[15] In brief, an alpaca and a dromedary were injected subcutaneously on days 0, 7, 14, 21, 28, and 35 with about 250 µg of human superoxide dismutase [Cu—Zn] (SOD1) per injection. After these six rounds of immunization, antibodies of different IgG subclasses were obtained by successive affinity chromatography on protein A and protein G columns. Total plasma and three purified IgG subclasses (IgG1, IgG2 and IgG3) from both alpaca and dromedary were tested by ELISA to assess the immune response to SOD1. In the dromedary, there was immune response in all IgG subclasses with best response in IgG1. The immune response raised in alpaca was very low. Two VHH libraries (one from the alpaca and one from the dromedary immunized with SOD1) were constructed using conventional methods[16, 17] and screened for the presence of SOD1-specific nanobodies. To this end, total RNA from peripheral blood lymphocytes was used as template for first strand cDNA synthesis with oligo(dT) primer. Using this cDNA, the VHH encoding sequences were amplified by PCR, digested with PstI and NotI, and cloned into the PstI and NotI sites of the phagemid vector pHEN4. From the alpaca, a VHH library of about $10^8$ independent transformants was obtained. About 74% of these transformants harbored the vector with the right insert size. In a similar way, from the dromedary, a VHH library of about $2.5 \times 10^8$ independent transformants was obtained. About 84% of the transformants from the dromedary library harbored the vector with the right insert size.

Each library was subject to four consecutive rounds of panning, performed on solid-phase coated antigen (concentration: 100 µg/ml, 10 µg/well). The enrichment for antigen-specific phages after each round of panning was assessed by comparing the number of phages eluted from antigen-coated wells with the number of phages eluted from only-blocked wells. The enrichment was also evaluated by polyclonal phage ELISA. Based on these assays, the library obtained from alpaca was enriched for antigen-specific phages only after the fourth round of panning. In contrast, the library from dromedary was enriched for antigen-specific phages after second, third, and fourth rounds, with best enrichment factors after second and third rounds.

From the alpaca library, 189 individual colonies identified after the fourth round of panning were randomly selected and analyzed by ELISA for the presence of SOD1-specific nanobodies in their periplasmic extracts. Out of 189 colonies, 129 scored positive in this assay. Sequencing of 46 of these positive colonies identified seven different nanobodies. All seven of these nanobodies belong to the same group.

From dromedary library, 142 individual colonies (47 from the second and 95 from the fourth round of panning) were randomly selected and analyzed by ELISA for their specificity for SOD1. Out of these 142 colonies, 64 colonies (42 from the second round and 22 from the fourth round) scored positive in this assay. Sequencing of 36 positive colonies identified seven different nanobodies representing three different groups. These vary only by single-point mutations away from the variable regions that are involved in antigen binding. These mutations are likely derived from PCR errors during construction of libraries. From these two libraries, one nanobody (Nb1) was selected from alpaca library, and three nanobodies (Nb2, Nb3, Nb4) were selected from dromedary library, each representing an individual group (Table 1). An alignment of all nanobodies is provided in FIG. 15.

TABLE 1

Overview of the obtained SOD1 nanobodies after the immunization and their characteristics.

| Name | Species | Number of nanobodies of the same isotype | $K_a$ (M) | $\Delta H$ (cal/mol) | $\Delta S$ (cal/mol/deg) |
|---|---|---|---|---|---|
| Nb1 | Alpaca | 7 | $7.9 * 10^5 +/- 3.5 * 10^6$ | $-1.1 * 10^4 +/- 0.2 * 10^4$ | $-17$ |
| Nb2 | Dromedary | 2 | $4 * 10^6 +/- 0.9 * 10^6$ | $-1.6 * 10^4 +/- 0.4 * 10^4$ | $-23$ |
| Nb3 | Dromedary | 4 | Non detectable | Non detectable | Non detectable |
| Nb4 | Dromedary | 1 | N/A | N/A | N/A |

These four constructs were expressed in *E. coli* by subcloning into BamHI/XhoI sites of pET30a (Novagen), to obtain His$_6$-tagged peptides. These were purified using conventional Ni-affinity purification protocol (Qiagen). Briefly, proteins were overexpressed in C41 (DE3) cells overnight at 25° C. in TB medium after induction with 1 mM IPTG. Cells were lysed by high-pressure cell cracker in lysis buffer (TBS containing 15 mM imidazole), and supernatant was cleared by centrifugation at 12,000 rpm for 20 minutes. Supernatant was incubated with Ni-agarose for 30 minutes, followed by washes with 200 volumes of lysis buffer, and eluted in TBS containing 250 mM imidazole. In a second step, nanobodies were purified by size-exclusion chromatography on SUPERDEX® S-75 columns in TBS buffer and concentrated using Centricon units (Millipore).

Isothermal Titration Calorimetrics

The heat of binding of selected nanobodies to SOD1 was measured using the Omega isothermal titration calorimeter (Microcal). Samples containing SOD1 in TBS were titrated with selected nanobodies in TBS in an isothermal chamber kept at the constant temperature of 25° C. Samples were filtered through 0.2 mM syringe and degassed before measurements. Aliquots (10 µL) of nanobodies were added consequently each 10 minutes (28 aliquots in total) to allow for the chamber to equilibrate. The resulting change in the heat required to equilibrate the chamber to the constant temperature was recorded and processed using the single-site binding equation[18] in the Origin 7.0 software (Microcal).

Transmission Electron Microscopy

The proteins for TEM studies were expressed in *E. coli* and purified as described above. Samples containing either SOD1 (0.2 mM) alone or SOD1 with equimolar concentrations of selected nanobodies were imaged after incubation for 4 weeks with shaking in 50 mM Tris-HCl (pH 8) at 25° C. Where indicated, DTT and EDTA were added to concentrations of 40 and 10 mM, respectively, to facilitate fibrillar aggregation of SOD1. Aliquots (5 µL) of the incubated protein preparations were adsorbed to carbon-coated FormVar film on 400-mesh copper grids (Plano GmbH, Germany) for 1 minute. The grids were blotted, washed twice in 50 µL droplets of MILLI-Q® water, and stained with 1% (wt/vol) uranylacetate (Sigma). Samples were studied with a JEOL® JEM-2100 microscope at 200 kV. Images were processed using iTEM software.

DNA Constructs and Manipulation

Coding DNA of SOD1 was amplified from human brain cDNA library (Invitrogen) and cloned into BamHI/XhoI sites of pCDNA4a (Invitrogen) to produce MycHis$_6$ tagged SOD1 construct for mammalian expression.[19] SOD1-CFP construct was prepared by subcloning of SOD1 from pCDNA4 into BamHI/XhoI sites of pCDNA3-CFP (Addgene #13030).

For zebrafish injections, a pcDNA plasmid containing full-length cDNA of wild-type or mutant (A4V) SOD1 behind a T7 promoter was linearized with Asp7181 and mRNA was transcribed in vitro using a mMESSAGE mMACHINE® T3 Kit (Ambion, Huntingdon, UK) followed by purification with a MEGAclear™ Kit (Ambion, Huntingdon, UK). The nanobody mRNAs were similarly produced using a mMESSAGE mMACHINE® T7 Kit (Ambion, Huntingdon, UK).

Expression vectors for human SOD1$^{WT}$ enhanced green fluorescent protein (EGFP), SOD1$^{G93A}$-EGFP, and SOD1$^{A4V}$-EGFP, that were used for NSC-34 transfection, were kindly donated by Prof. Esquerda from Universitat de Lleida, Spain.

Nanobody (Protein) Production

The SOD1 nanobody protein was produced by the Protein Service Facility of VIB (Gent, Belgium). A His tag was added to better detect it, followed by a mCaspase-3 recognition site to remove the fusion partner. The protein sequence of the nanobody without initial methionine and the tags is:

(SEQ ID NO: 1)
QVQLQESGGGSVQAGGSLRLACVASGGDTRPYITYWMGWYRQAPGKEREG

VATIYTGGSGTYYSDSVEGRFTISQDKAQRTVYLQMNDLKPEDTAMYYCA

AGNGALPPGRRLSPQNMDTWGPGTQVTVSS.

To remove the His-tag, Caspase-3 (RD Systems) was added to the nanobody and it was incubated overnight at 37° C. Using His Select Niguel Magnetic Agarose Beads (Sigma), the His-tag could be separated from the nanobody.

Cell Culture

Human carcinoma (HeLa) cell lines were obtained from the American Type Culture Collection (ATCC) and cultured according to standard mammalian tissue culture protocols in Dulbecco's Modified Eagle Medium supplemented with 10 mM Hepes buffer. All media were supplemented with 10% FBS, 100 units/ml penicillin and 100 µg/ml streptomycin/2 mM L-glutamine. All tissue culture media and supplements were obtained from Difco. Cells were transfected using Fugene (Roche) according to the manufacturer's protocol. In a typical transfection, $2 \times 10^5$ cells were transfected with 1 µg of DNA dissolved in 100 µl of DMEM.

The mouse motor neuron-like hybrid cell line NSC-34 (hybrid cell line produced by fusion of motor neuron enriched, embryonic mouse spinal cord cells with mouse neuroblastoma[20] was purchased from CELLutions Biosystems (Toronto, Canada). Cells were subcultured in 6-well plates ($2 \times 10^5$ cells per well) and transiently transfected with plasmids (10 µg DNA per well) using a 1:1 ratio of LIPO- FECTAMINE® 2000 (Invitrogen, Gent, Belgium) to DNA. Expression vectors for human SOD1$^{WT}$-EGFP, SOD1$^{G93A}$-EGFP, and SOD1$^{44V}$-EGFP were used for transfection. Cells were fixed at 24 to 72 hours with 4% paraformaldehyde and permeabilized with PBS 0.1% TRITON® X-100, blocked in normal goat serum and incubated overnight at 4° C. in goat anti-HA or rabbit anti-His antibody (1/500). Immunoreactivity was visualized after incubation with Cy5-conjugated anti-goat secondary antibody 1/500 in PBS from Invitrogen (Carlsbad, Calif.) under a Fluorescence microscope (DMIRB; Leica) or Confocal microscopy (Zeiss 200M microscope, Munich, Germany).

Zebrafish Maintenance and Embryo Injection

All experiments were approved and performed in accordance with the guidelines of the Ethical Committee for Animal Experimentation, K. U. Leuven. Adult zebrafish (*Danio rerio*, AB strain) and embryos were maintained under standard laboratory conditions. Zebrafish embryo microinjections were made using a FemtoJet injection setup (Eppendorf, Hamburg, Germany). Each injection was made in the 1-4 cell stage of the zebrafish embryo and involved delivery of 2.14 nl of 1 μg/μl of SOD1 mRNA, accomplished by an injection pressure of less than 4.5 psi, which produced a droplet diameter of 160 μm on a micrometer. Embryos were co-injected with mRNA encoding the anti-SOD1 nanobody or a Control nanobody raised against another protein (β-lactamase) at concentrations ranging from 0.25 to 25 ng/μl. Embryos were then stored in Danieau water (50 mM NaCl, 0.7 mM KCl, 0.4 mM MgSO$_4$.7H$_2$O 0.6 mM Ca(NO$_3$)2.4H$_2$O, 0.5 mM HEPES) at 27.5° C. to 28.5° C.

Analysis of Motor Neuron Outgrowth

At 30 hours post-fertilization (hpf), morphologically normal zebrafish embryos were fixed in 4% paraformaldehyde in phosphate-buffered saline (PBS) and immunostained using mouse anti-synaptic vesicle 2 (1/200; Developmental Studies Hybridoma Bank) and secondary ALEXA FLUOR®-555 anti-mouse antibody (1/500; Molecular Probes) in order to visualize motor neurons. Observers blind to injection and treatment conditions measured the axonal length of the first five ventral motor axons after the yolk sac in each embryo using Lucia software (PSI, version 4.9) and the average of these five lengths was calculated for each embryo.

Electrophoresis and Western Blotting

Protein lysates were prepared from zebrafish embryos following removal of the protein-rich yolk sac by triturating within a thin-tipped glass pipette. The embryos were then lysed in T-PER buffer and homogenized using a manual dounce.

Cell medium was removed from the cell culture and cells were washed with PBS and harvested. Cells lysates were obtained by adding T-PER buffer and homogenizing by pipetting.

Protein concentrations were determined using the microBCA protein assay reaction kit 207 (Pierce, Rockford, Ill.). Samples were separated according to size through denaturing 10% sodium dodecyl sulphate-polyacrylamide gel electrophoresis (SDS-PAGE). An equal amount of protein from each sample was heated at 100° C. for 5 minutes with an equivalent volume of sample buffer (containing 8% SDS and 2% mercaptoethanol) and loaded onto polyacrylamide gels. The proteins were electro-transferred to a PVDF membrane in Tris-glycine-methanol buffer. The membrane was blocked for 1 hour at room temperature (RT) in a blocking solution mixture of 5% nonfat dry milk, 0.1% TWEEN® 20, and TBS. The membrane was then incubated for 2 hours at RT with primary antibody (1/1000 anti-SOD1, Sheep pAB, Cal-biochem-Merck Chemicals, 1/1000 anti-SOD1, rabbit pAb, Stressgen, 1/1000 anti-HA goat pAB, Abcam, Cambridge, UK, 1/5000 anti β-actin mAB, Sigma-Aldrich, 1/1000 anti-Hsp70, mouse pAb, Stressgen). The membrane was rinsed once with TBS-TWEEN® 20 for 15 minutes, washed twice with blocking solution for 5 minutes, and then incubated for 1 hour at RT in peroxidase-labeled secondary antibodies from Santa Cruz Biotechnology (1/5000, Santa Cruz, Calif.). The blot was washed once for 15 minutes, once for 10 minutes, and three times for 5 minutes, and then processed for analysis using a SUPERSIGNAL® chemiluminescent detection kit (Pierce), as described by the manufacturer, and a BioRad GELDOC® System.

Immunocitochemistry

Mice were anesthetized using 10% pentobarbital sodium in PBS. After transcardiac perfusion with ice-cold PBS followed by fixation with 4% paraformaldehyde, spinal cords were dissected and post-fixed for 2 hours in 4% paraformaldehyde. Spinal cord sections (16 μm) were cut on a cryostat (Leica, Wetzlar, Germany), and mounted in gelatinized slides. Samples were incubated in PBS with 0.1% TRITON® X-100 (PBST) and blocked in PBST with 10% normal donkey serum (Sigma, St Louis, Mo.) for 1 hour. The following primary antibodies were used: mouse anti-NeuN (Millipore, Billerica, Mass.), and rabbit anti-P2X$_4$ (Alomone Labs, Jerusalem, Israel). Antibodies were incubated overnight at 4° C. After three washing steps, the samples were incubated with the corresponding secondary antibodies (ALEXA FLUOR® 555 or ALEXA FLUOR® 488; Invitrogen). After three washing steps, sections were mounted using Vectashield (Vector Laboratories, Burlingame, Calif.) (with 4',6-diamidino-2-phenylindole) and analyzed under a fluorescence microscope (DMIRB; Leica).

Immunoprecipitation

Samples were centrifuged in a microcentrifuge for 10 minutes at 12,000 rpm and at a temperature of 4° C. and then placed on ice. The supernatant was aspirated and placed in a fresh tube, then kept on ice and incubated with the antibody (1/1000 anti-SOD1, Calbiochem) overnight at 4° C., under agitation. The protein A Sepharose beads (Amersham Pharmacia Biotech AB) were used to immunoprecipitate. The lysate-beads mixture was incubated at 4° C. under rotary agitation for 4 hours. After that, the samples were centrifuged, the supernatant was collected, and the beads were washed in lysis buffer three times. Finally, the last supernatant was removed, 25 μl of 2× loading buffer was added to the beads, and both the first collected supernatant and the samples were boiled at 95° C.-100° C. for 5 minutes for ulterior SDS PAGE and Western blot.

Treatment and Evaluation of Mice

Adult mice overexpressing human SOD1$^{G93A}$ (C57BL/6 background) were maintained in accordance with the Guide of Care and Use of Experimental Animals of the Ethical Committee of KU Leuven. The Ethical Committee of KU Leuven approved all animal experiments. The experiments were littermate and gender matched. At post-natal day 60 (P60), P90 and P120, the intracerebroventricular administration of the nanobody (three times a week) and the evaluation of the injected mice were started. The mice were weighed and the hanging wire test and the rotarod treadmill (Ugo Basile, Comerio, Italy) were used to evaluate the motor performance. For the hanging wire test, each mouse was given three trials of 60 seconds, two times a week. For rotarod treadmill, mice had to walk at 15 r.p.m over the course for 180 seconds. Each mouse was given three trials of 180 seconds, two times a week. The mice were killed when they could no longer roll over within 20 seconds after being placed on their backs, and thus considered this time point as the time of death.

Intracerebroventricular Cannulation in Mice

Before surgery, animals were anesthetized by isoflurane inhalation. Following anesthesia, the fur was shaved from the top of the skull, and the mouse scalp was disinfected with ethanol. The animal was then positioned on the stereotaxic apparatus, the head was fixed using nonrupture ear bars and a 2-cm midsagittal skin incision was made on the scalp in order to visualize the skull landmarker bregma (formed by the cross of the coronal and sagittal sutures). A microdrill was used to perform a small hole (1 mm of diameter) on the left side of the skull according to the previously defined stereotaxic intracerebroventricular coordinates: Anteroposterior=−0.1 mm; Mediolateral=+1.0 mm (left side), from bregma. Stereotaxic coordinates were determined from the mouse brain atlas (George Paxinos and Keith B. J. Franklin, Academic Press, 2005). Localization of the final point of injection was previously confirmed by injection of 1 microliter of colorant (Coomassie blue) in a small subgroup of animals. A stainless steel guide cannula with a tubing below the pedestal of 3 mm (Bilaney, Dusseldorf, Germany), was inserted into the hole made previously. The cannula was firmly cemented to the skull with dental cement. Then, the skin was sutured with a non-absorbable, sterile, surgical silk suture. Finally, the animal was kept warm on a temperature-controlled heating pad (~37° C.) until its full recovery.

Motoneurons and Neuromuscular Junctions Counting

Gastrocnemius muscle was snap-frozen in isopentane, cooled by immersion in liquid nitrogen. Cryostat sections (20 μm) were stained with hematoxylin and eosin (H&E), modified Gomori trichrome and nicotinamide adenosine dinucleotide (NADH)-tetrazolium reductase. To visualize neuromuscular junctions, longitudinal cryostat sections (40 μm) were immunostained with NF-200 (1:200, Sigma, N4142), and ALEXA®-488-conjugated α-bungarotoxin (1:500, Invitrogen, B13422). To perform cresyl violet (Sigma) on spinal cord, fixed (4% paraformaldehyde), dehydrated (30% sucrose) and snap-froze spinal cord were fixed in Tissue-Tec (Sakura) and then made cryostat sections of 20 μm thickness. The area of normal-appearing neurons in the ventral horn of the lumbar spinal cord was calculated on every tenth slide for a total of ten slides per animal using Axiovision 4 software (Zeiss) and determined the number of neurons in different size groups. Neurons in the ventral horn of the lumbar spinal cord, with a cell body area>250 μm$^2$, were considered motor neurons.

SOD1 Activity

NSC-34 cells were cultured, transfected with EGFP-SOD1 and treated with nanobody as described before. After 48 hours of culture, dismutase activity was determined (Cell Biolabs, San Diego, Calif.) as described by the manufacturer.

Statistics

Data are shown as mean±SEM. Student-t test was used to calculate significance. When more than two groups were compared, a one-way analysis of variance with Tukey least significant difference post hoc test was used.

Example 1

Generation and Characterization of Single-Domain Antibodies Against SOD1

SOD1 Nanobodies (Nucleic Acids) have High Affinity for SOD1 In Vitro

Figure 1B:
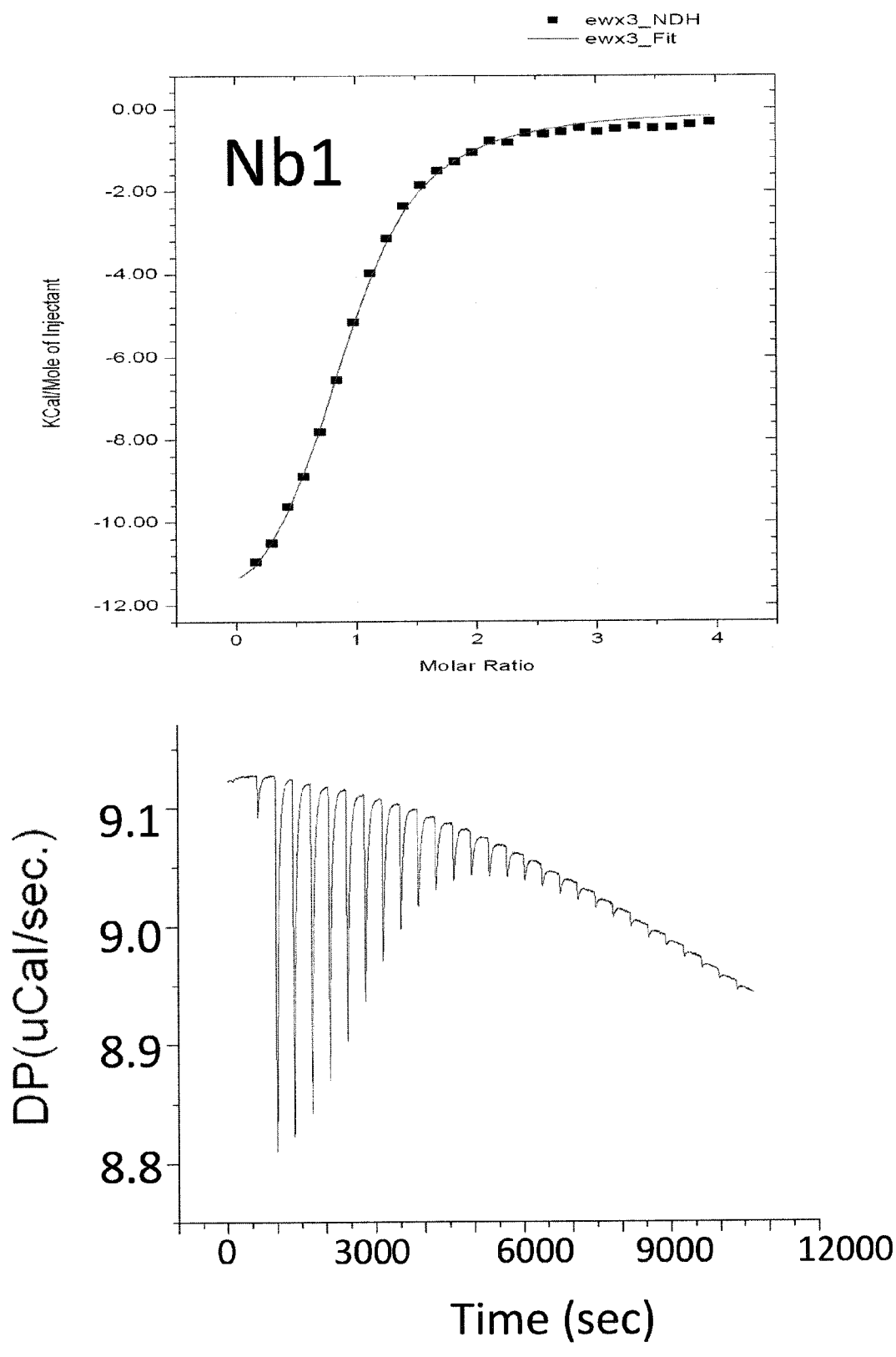
Figure 1B:
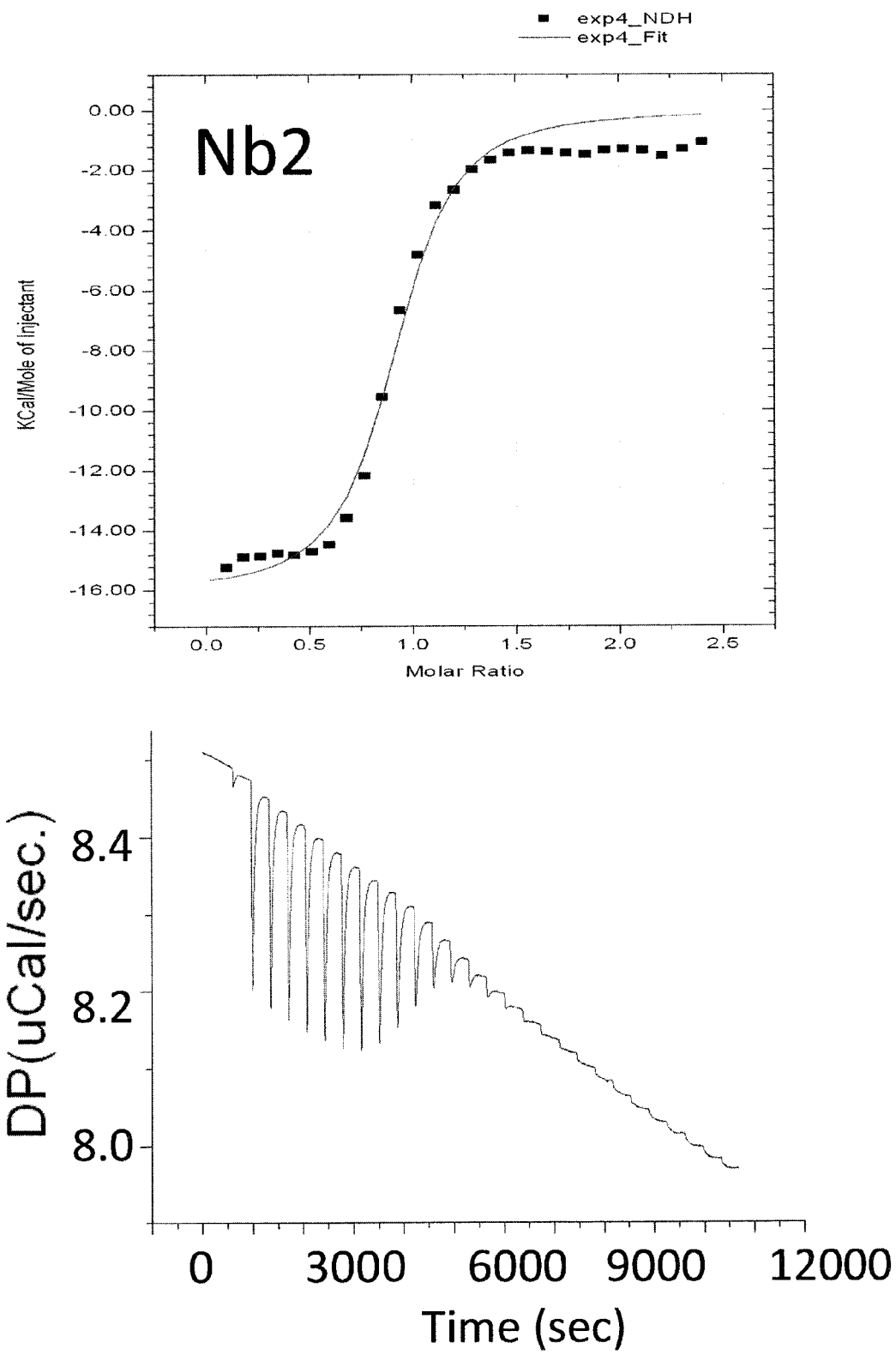

The binding of nanobodies to immobilized recombinant SOD1 was verified by Western Dot Blot (FIG. 1A). Strong binding was detected with Nb1 and Nb2, but not the Nb3 and Nb4, suggesting that the recombinant Nb3 was not fully active. To further characterize the binding properties of the nanobodies, Isothermal Titration calorimetry (ITC) was performed to determine affinities (Kd), enthalpies (ΔH) and entropies (ΔS) of binding.[18] Solution containing SOD1 was titrated with nanobodies in an isothermic chamber at 25° C., and the heat required to dissipate the energy of binding was recorded for each titration (FIG. 1B, lower panel). These data were fitted into one-site binding model to calculate affinity of binding Kd, ΔH and ΔS (FIG. 1B, upper panel). Both Nb1 and Nb2 were found to bind SOD1 with near-micromolar Kd: ~1 μM and ~0.2 μM for Nb2 and Nb1, respectively (Table 1 and FIG. 1B). The high enthalpy of interaction (−15 kCal per mole) indicated efficient binding for both nanobodies. Calculation of Kd and thermodynamic parameters of binding for Nb3 was not possible due to its low affinity and limitations on the amount of the ligand.

SOD1 Nanobodies (Nucleic Acids) Block Fibril Formation by SOD1

Figure 1C:
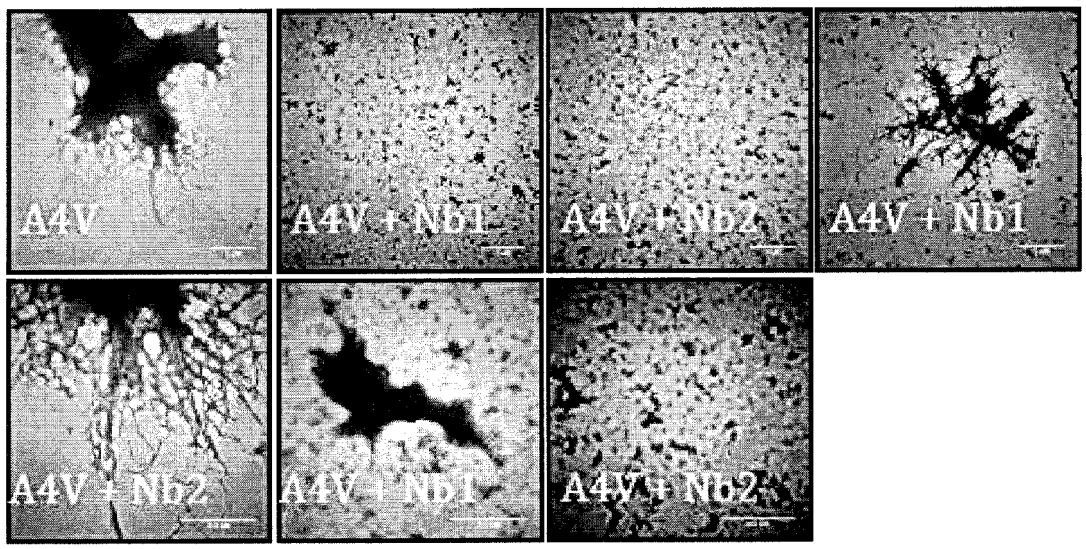
Figure 1D:
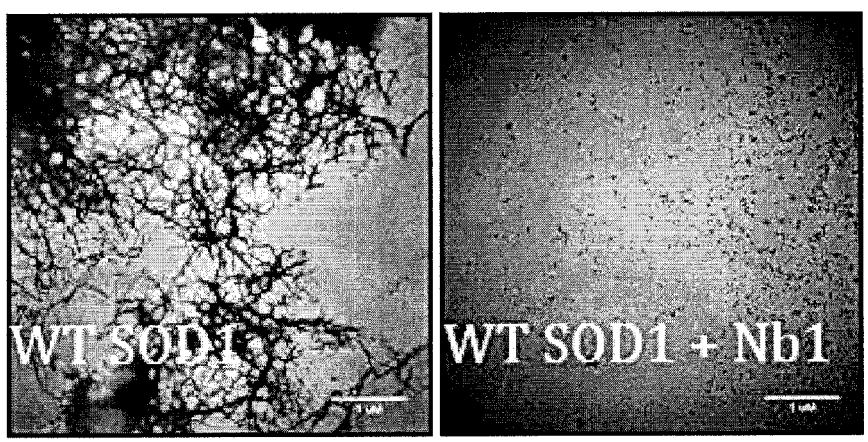

To determine if nanobodies can affect SOD1 aggregation in vitro, formation of fibrils by SOD1 in the presence of nanobodies was characterized by Transmission Electron Microscopy (TEM). It has been previously shown that SOD1 forms amyloid fibrils in conditions where binding of metal ions and assembly of SOD1 dimer is compromised by addition of Guanidinium Chloride or disulfide reducing agents and EDTA.[21] Thus, TEM was used to probe formation of amyloid fibrils by SOD1 destabilized by addition of DTT and EDTA. Both SOD1 WT (not shown) and A4V mutant very efficiently formed visible precipitates under these conditions that consisted entirely of amyloid fibrils as seen by TEM (FIG. 1C). The appearance of SOD1 fibrils was similar to that of previously published studies, and no amorphous aggregates were observed under these conditions. However, in the presence of equimolar concentrations of Nb2, formation of amyloid fibrils was completely suppressed, resulting in the formation of small or amorphous aggregates (FIG. 1C). This result suggests that binding of Nb2 interferes with formation of cross-beta structure by destabilized SOD1, probably through steric or conformational hindrance. Nb1 was less effective in suppression of amyloid formation by SOD1, as aggregates were mainly amorphous, but also contained some amyloid fibrils (FIG. 1C). This result might reflect difference in Kd of Nb1 and Nb2 for SOD1, as well as a difference in binding sites on SOD1. To determine if Nb1 can block SOD1 fibril formation under less stringent conditions, it was incubated with the non-destabilized SOD1 in 50 mM Tris, pH 8.0 for 1 month with shacking at 25° C. In these conditions, SOD1 can form both amorphous and amyloid fibrils, but fibril formation is very inefficient as most of the protein stays soluble in the solution. Indeed, formation of some SOD1 fibrils by TEM was observed under these conditions, although no visible precipitate was formed (FIG. 1D). By contrast, no aggregates could be seen by TEM in samples containing both Nb1 and SOD1. Hence, it was concluded that both Nb1 and Nb2 can suppress formation of fibrils by SOD1 in vitro.

SOD1 Nanobodies (Nucleic Acids) Reduce SOD1 Aggregation in HeLa Cells

To determine the effect of the nanobodies on aggregation of SOD1 in cell culture, the nanobodies were expressed as HA-tagged or HA-Myc-His$_6$ tagged constructs in HeLa cells (FIG. 2A). Initially, pull-down of HA-Myc-His$_6$ tagged nanobodies (Nb1, Nb2, Nb3 and Nb4) was performed to ensure that the nanobodies expressed in mammalian cells retain binding capacity for SOD1. HeLa cells were transiently co-transfected with Nb1, Nb2, Nb3 and Nb4 and SOD1-CFP, lysed and nanobodies were purified on Ni-agarose as described in Materials and Methods. SOD1-CFP was co-purifying together with Nb1, Nb2 and Nb3, indicating that they bind SOD1 efficiently when expressed in HeLa cells (FIG. 2A).

The oligomeric state of SOD1$^{A4V}$ co-expressed with the nanobodies in transiently transfected HeLa cells was analyzed by Blue Native Polyacrylamide gel electrophoresis (BN-PAGE) following lysis under non-denaturing conditions in non-ionic detergent MPER buffer in order to preserve intracellular aggregates. While most A4V migrated as monomers and dimers in a bottom part of BN-PAGE, some of it formed a smear that extended to the upper limit of fractionation on the gel (several thousand kDa), indicating formation of high molecular weight (HMW) oligomeric species of A4V FIG. 2C). By contrast, in lysates of cells co-transfected with A4V and Nb1 or Nb2, A4V was migrating entirely as low molecular weight oligomers (FIG. 2C).

This data demonstrates that Nb1 and Nb2 inhibit aggregation of SOD1$^{A4V}$, with the Nb2 being the most effective. Therefore, the effect of this nanobody in mutant SOD1-associated disease models was further investigated.

Example 2

Figure 3A:
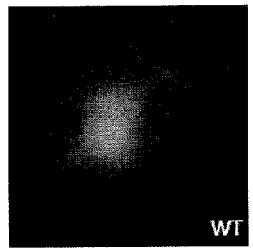
FIGS. 3A-3E: SOD1 aggregates formation and HA-tagged nanobody expression after transient transfection in NSC-34 cells. 24 hours after transfection, mutant SOD1 aggregates could be observed when cells were transfected with (FIG. 3B) eGFP-SOD1$^{G93A}$ and (FIG. 3C) eGFP-SOD1$^{A4V}$ but not with (FIG. 3A) eGFP-SOD1$^{WT}$. Control and SOD1 nanobodies could be detected by IHQ (FIG. 3D) and Western blot (FIG. 3E) after transfection through the HA-tag.
Figure 3B:
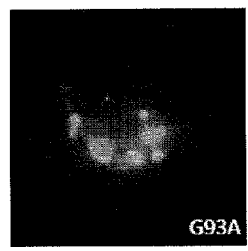
Figure 3C:
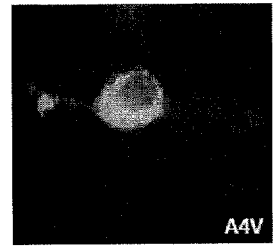
Figure 3D:
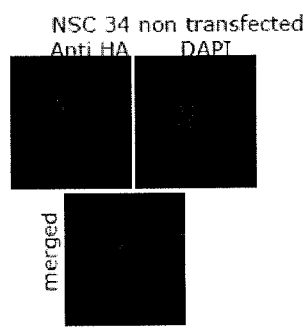
Figure 3D:
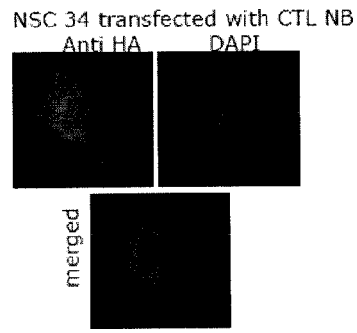
Figure 3D:
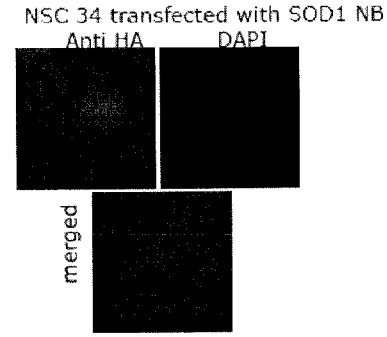
Figure 3E:
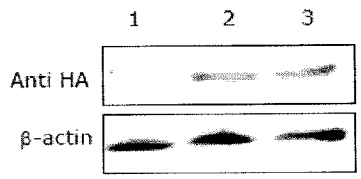
Figure 4A:
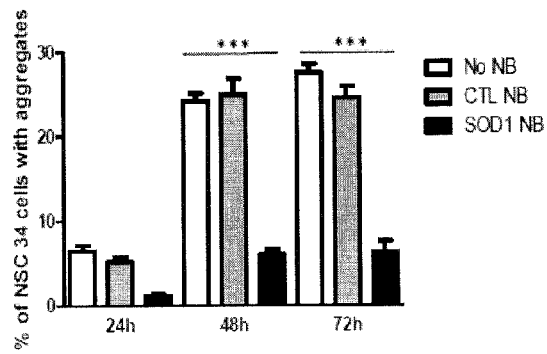
FIGS. 4A-4C: SOD1 nanobody reduces the number of cells with mSOD1 aggregates after transfection. After SOD1 nanobody and mSOD1 co-transfection in NSC-34 cells, SOD1 nanobody reduces the number of cells with SOD1$^{G93A}$ (FIG. 4A) and SOD1$^{A4V}$ (FIG. 4B) aggregates. This reduction is dose dependent (FIG. 4C). The appearance of the aggregates could vary between the different mutations without any apparent correlation, and the SOD1 nanobody also did not affect this appearance.
Figure 4B:
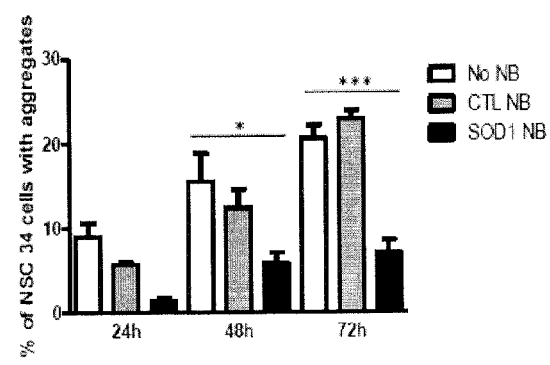
Figure 4C:
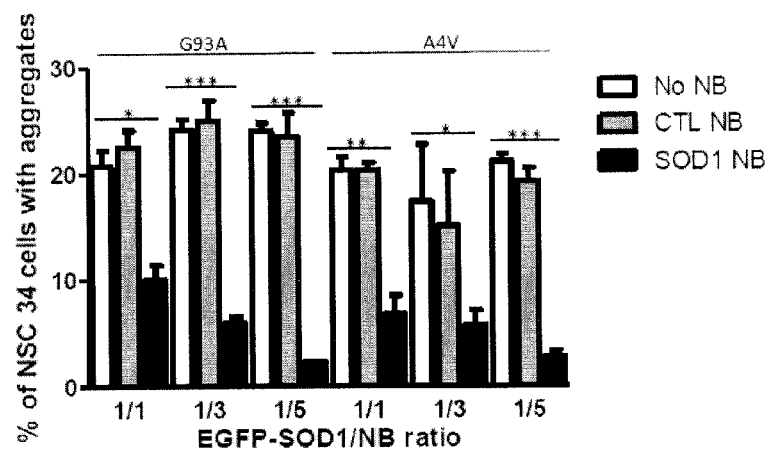

SOD1 Nanobody (Nucleic Acids) Abolishes Mutant SOD1 Aggregate Formation in NSC34 Cells Transfection of the SOD1 Nanobody Abolishes Mutant SOD1 Aggregate Formation in NSC-34 Cells The effect of the expression of the HA-tagged anti-SOD1 nanobody on the formation of mutant SOD1-induced aggregates in motor neuronal NSC-34 cells was investigated. Transfection of NSC-34 cells with mutant (AV4 and G93A) but not WT SOD1-eGFP induced the formation of cytoplasmic mutant SOD1 aggregates, as has been described before (FIGS. 3A, 3B and 3C). First, the nanobody expression after transfection was tested by immunocitochemistry and Western blot (FIGS. 3D and 3E). The effect of nanobody expression on aggregate formation by co-transfecting NSC-34 cells with SOD1-eGFP and either the SOD1 nanobody or control nanobody was assessed (FIGS. 4A-4C). The number of NSC-34 cells containing aggregates was quantified 24, 48 and 72 hours after transfection (FIGS. 4A and 4B). Expression of the anti-SOD1 nanobody, but not of the control nanobody, significantly decreased the number of cells with aggregates induced by both SOD1$^{G93A}$-EGFP (FIG. 4A) and SOD1$^{A4V}$-EGFP (FIG. 4B). Increasing the ratio of SOD1 nanobody/mutant SOD1-EGFP cDNA, demonstrated this effect to be dose-dependent (FIG. 4C).

By performing immunoprecipitation on cell lysates from the NSC-34 transfections, it was demonstrated that the anti-SOD1 nanobody, but not the control nanobody, binds to SOD1 in co-transfected cells, as is shown in FIGS. 5A and 5B. The anti-SOD1 nanobody was not specific for mutant SOD1 as also SOD1$^{WT}$ and endogenous SOD1 was immunoprecipitated.

Figure 5C:
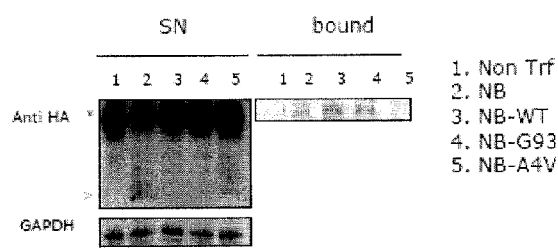
Figure 5C:
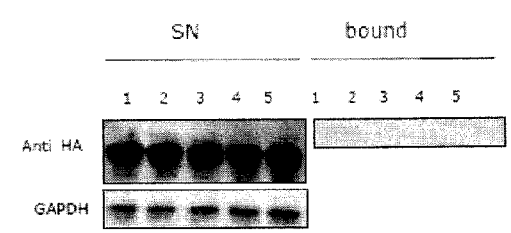
Figure 5C:
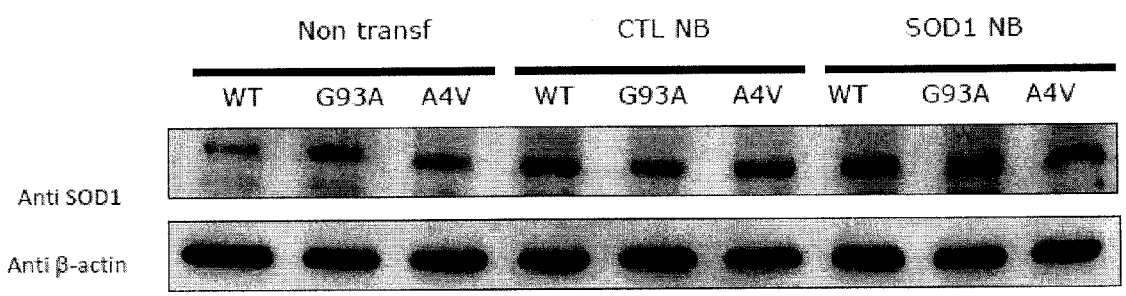

SOD1 levels were checked after SOD1 nanobody and eGFP-SOD1 co-transfection and could be seen that protein levels remained unaltered despite the reduction of the number of cells with aggregates and the recognition and specificity of the SOD1 nanobody for SOD1 (FIG. 5C). Chaperone levels were also checked but no variation was observed (data not shown).

Example 3

Figure 6A:
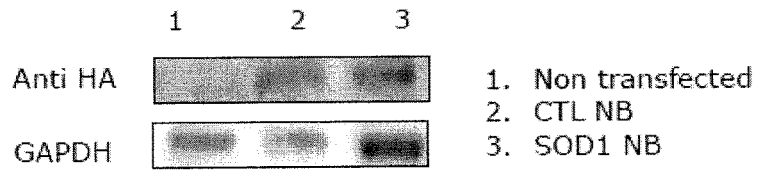
FIGS. 6A-6C: SOD1 nanobody reduces SOD1$^{A4V}$ protein level and abolishes its toxicity in zebrafish.

The SOD1 Nanobody (Nucleic Acids) Clears SOD1 and Rescues the Axonopathy in Zebrafish In Vivo The SOD1 Nanobody Clears SOD1 and Rescues the Axonopathy in Zebrafish In Vivo Expression of human mutant SOD1 or mutant TDP-43 induces axon outgrowth defects and aberrant branching in zebrafish.[22, 23] This model has been used for identification of disease modifiers in animal models and humans.[24] In order to investigate the effect of the anti-SOD1 nanobody on the mutant SOD1-induced axonopathy, zebrafish embryos were injected with mutant SOD1$^{A4V}$ mRNA with anti-SOD1 nanobody or control nanobody mRNA. First, nanobody expression was checked after nanobody mRNA injection in zebrafish by Western blot (FIG. 6A).

Figure 6B:
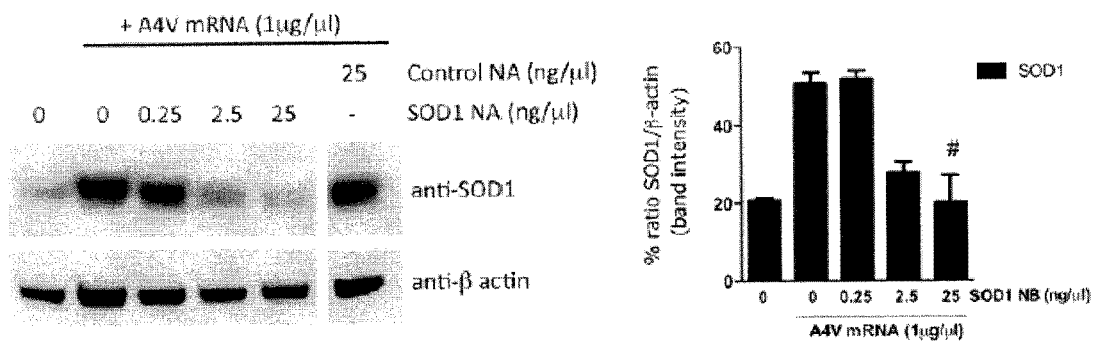

SOD1 immunoblot analysis revealed that co-expression of the anti-SOD1 nanobody decreased SOD1 levels in a dose-dependent manner (FIG. 6B), with 25 ng/µl achieving a significantly decreased SOD1 level (p=0.022). Injection of the control nanobody had no effect on SOD1 levels.

Figure 6C:
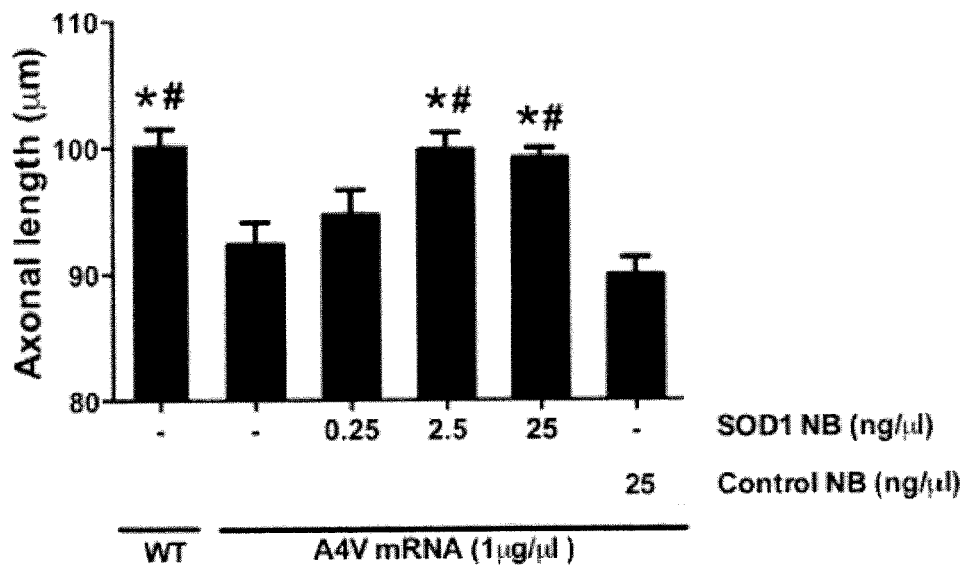

To evaluate whether the SOD1 nanobody rescued the axonal phenotype induced by mutant SOD1, the axonal length of motor neurons was measured at 30 hpf. Overexpression of SOD1$^{A4V}$ induced clear motor axonal abnormalities compared to overexpression of SOD1$^{WT}$ (p=0.0011), as described previously.[22] This axonopathy was rescued when fish were co-injected with the SOD1 nanobody (2.5 to 25 ng/µl, p<0.0031), but not the control nanobody (FIG. 6C).

Example 4

Figure 7A:
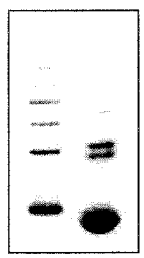
FIGS. 7A-7D: The SOD1 nanobody (protein) co-localizes with mutant SOD1 aggregates.
Figure 7B:
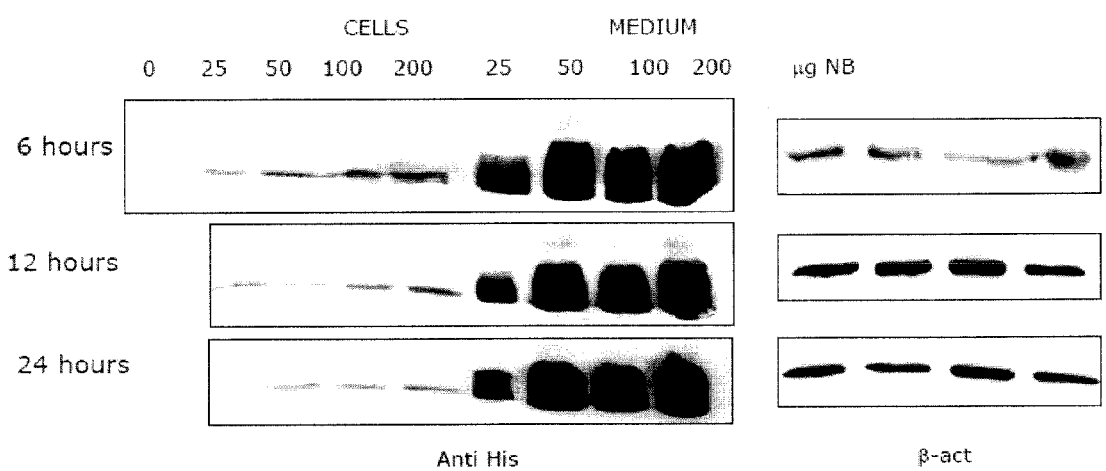

The SOD1 Nanobody (Protein) can Enter the Cell, Reduce the Number of Transfected NSC-34 Cells with SOD1 Aggregates and Rescue the Axonopathy in Zebrafish In Vivo The SOD1 Nanobody can Enter the Cell and Reduce the Number of Cells with SOD1 Aggregates Next, testing of the SOD1 nanobody in its protein form was desired. First, the detection of the SOD1 nanobody was tested through its His tag. Blotting pure SOD1 nanobody with an anti-His tag antibody, a thick band at the predicted molecular weight (~15 KDa) was seen, along with some other thinner bands corresponding to the dimerization or trimerization of the nanobody (FIG. 7A). To assess whether the SOD1 nanobody could cross the cell membrane and enter the cell, NSC-34 cells were cultured and different doses of SOD1 nanobody were added to the medium. After blotting the cells and the concentrated medium with the anti-His antibody, the nanobody could be detected in the medium and also associated with the cells (FIG. 7B).

Figure 7C:
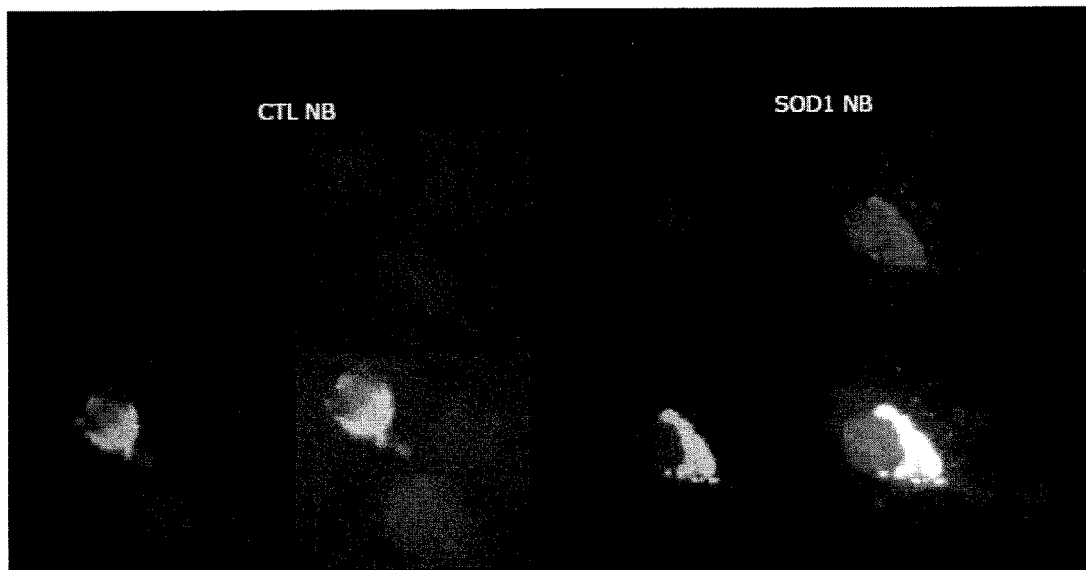
Figure 7D:
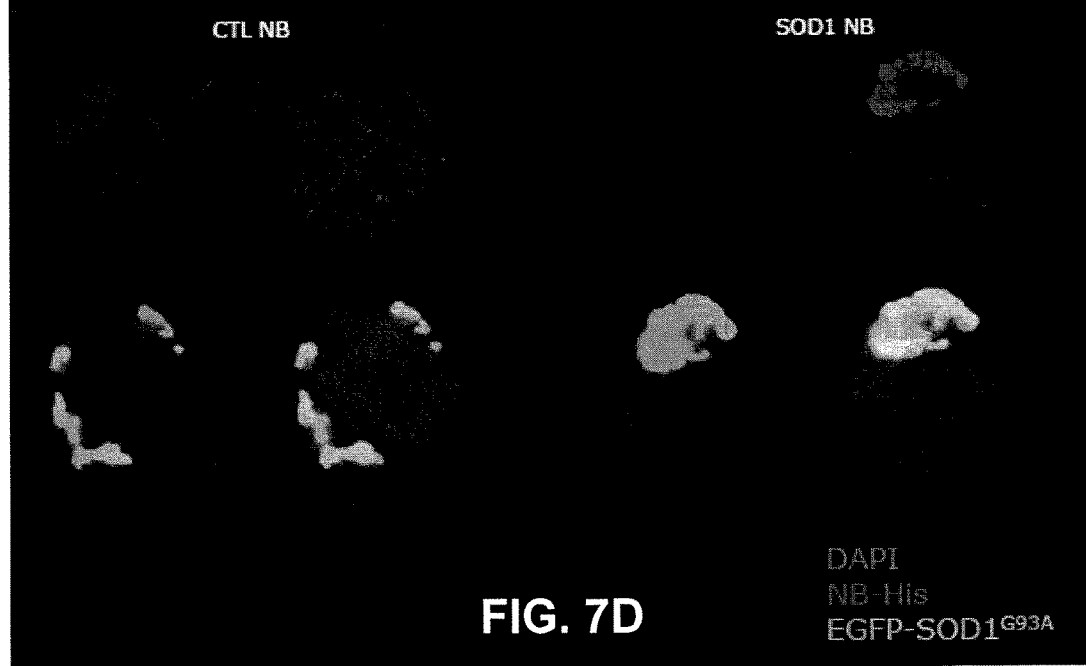

To confirm that the SOD1 nanobody was really inside the cell, NSC-34 cells were transfected with eGFP-SOD1$^{G93A}$ and then 50 µg/µl of nanobody was added to the culture medium. After processing the samples for immunocytochemistry, it was observed by fluorescence (FIG. 7C) and confocal (FIG. 7D) microscopy that the SOD1 nanobody, but not the control nanobody (nanobody protein against lysozyme), was co-localizing with mutant SOD1 aggregates.

When the transfected cells were fractionated and blotted, immunoreactivity for the anti-His antibody appeared in the cytosolic fraction only in treated cells (FIG. 8A), and SOD1 and SOD1 nanobody (through the His-tag) were co-immunoprecipitated (FIG. 8B).

To demonstrate the effect of the SOD1 nanobody in vitro, NSC-34 cells were transfected with eGFP-SOD1$^{G93A}$ and then different doses of the SOD1 nanobody were added to the medium. 48 hours after transfection and treatment, the number of cells were quantified with aggregates (FIG. 8C). A reduction of the number of transfected cells with aggregates in a dose-dependent way were seen only when the cells were treated with the SOD1 nanobody, but not when the cells were not treated or treated with the control nanobody. By contrast, when the SOD1 nanobody was added to the medium 48 hours after transfection, once the aggregates were formed, the SOD1 nanobody could not decrease the number of cells with aggregates (data not shown).

As the SOD1 nanobody has a mCaspase-3 sequence to remove the fusion tag from the nanobody, the SOD1 nanobody was incubated with Caspase-3 and then the His tag was separated from the pure nanobody and the transfected cells were treated. 24 hours after, the number of cells with aggregates were quantified. When the cells were treated with SOD1 nanobody pre-incubated with Caspase-3, with the His fraction or with the nanobody fraction, the number of cells with aggregates did not decrease (FIG. 8D), showing that the entrance of the nanobody to the cell was due to the His tag.

The SOD1 Nanobody Reduces SOD Activity in Transfected NSC-34 Cells

Figure 9:
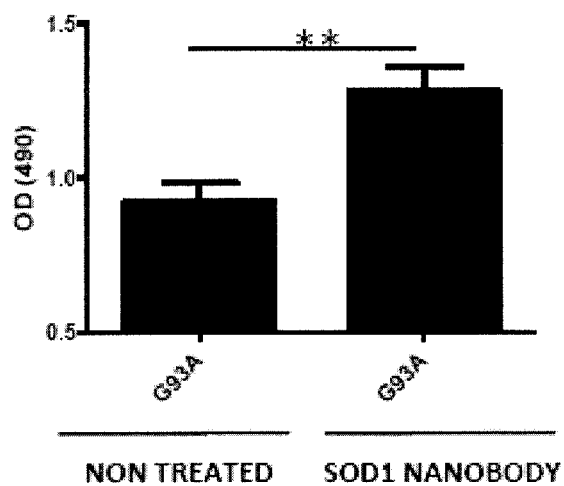
FIG. 9: The SOD1 nanobody reduces SOD activity. When the SOD1 nanobody is added to the cell medium, the SOD activity is decreased. Read-outs are OD values, inversely correlated with SOD activity (using OxiSelect™ Superoxide Dismutase Activity Assay of Cell Biolabs).

The assay principle, as described by the manufacturer, is that Superoxide anions (O2−) are generated by a Xanthine/Xanthine Oxidase (XOD) system, and then detected with a Chromagen Solution, provided by the kit. However, in the presence of SOD, these superoxide anion concentrations are reduced, yielding less colorimetric signal. Thus, more colorimetric signal means less SOD activity. When NSC-34 cells were transfected with eGFP-SOD1, those that were treated with the SOD1 nanobody showed less SOD activity (FIG. 9), giving evidence for the binding of the SOD1 nanobody and the SOD1 protein.

Effect of the SOD1 Nanobody in the Zebrafish Model for ALS

Figure 10:
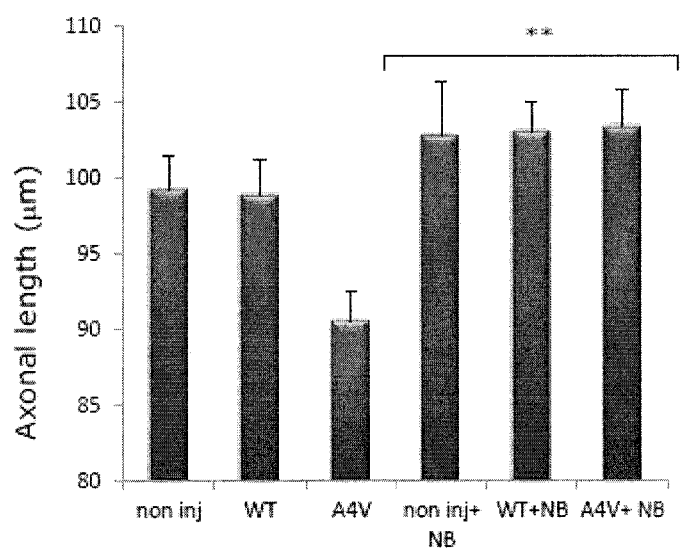
FIG. 10: Effect of the SOD1 nanobody treatment in injected zebrafish. The SOD1 nanobody can increase the axonal length and rescue the phenotype induced by mutant SOD1 in injected zebrafish when added to the tank water.

As described previously, zebrafish is a good model to investigate ALS pathogenesis and possible treatments. The zebrafish were injected with mutant SOD1 and 3 hours later, SOD1 nanobody was added to the tank water. Thirty hours post-fertilization, the zebrafish were fixed and then axonal length was measured. SOD1 nanobody could rescue the axonal length in injected zebrafish when added directly to the tank water (FIG. 10).

Example 5

Figure 11A:
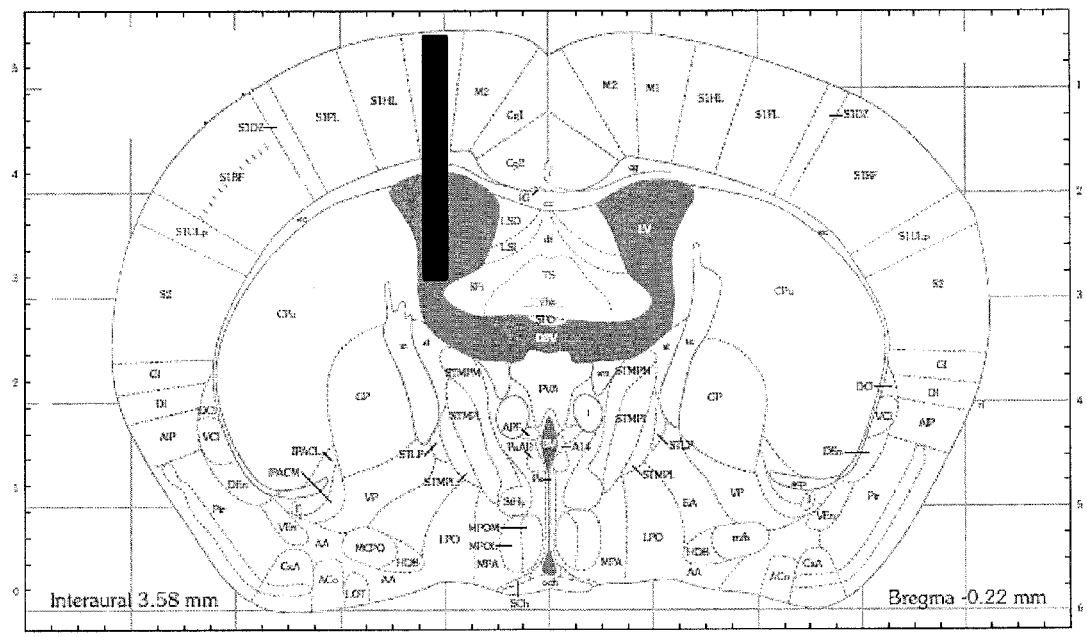

The SOD1 Nanobody (Protein) Prevents Motoneuron Death, Delays Disease Onset and Prolongs Lifespan in a Mouse Model for ALS Effect of the SOD1 Nanobody in a Mouse Model for ALS As mutant SOD1 has been described as a cause of ALS, testing the SOD1 nanobody in a well-established mouse model for ALS was desired. Therefore, the ALS mouse model overexpressing human mutant SOD1 (SOD1$^{G93A}$) was used. The administration of the nanobody was performed intracerebroventricular through an implanted cannula (FIG. 11A).

Figure 11B:
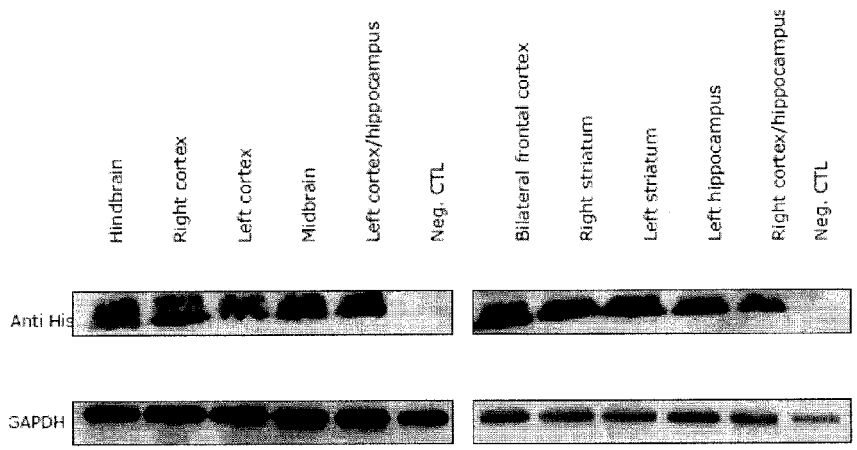

To test whether the nanobody was correctly injected and could reach different parts of the central nervous system (CNS), 2 μl (7 μg/μl) were injected, and then 2 hours later, different parts of the brain and spinal cord were dissected. As a negative control, the whole brain and spinal cord of a non-injected mouse was used. As shown in FIGS. 11B and 11C, the nanobody was detectable in different structures of the brain (FIG. 11B) and spinal cord (FIG. 11C), whereas no signaling was detected in the negative control.

Figure 11D:
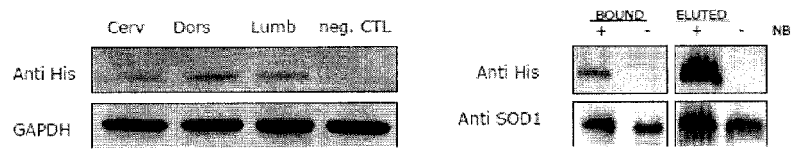
Figure 11D:
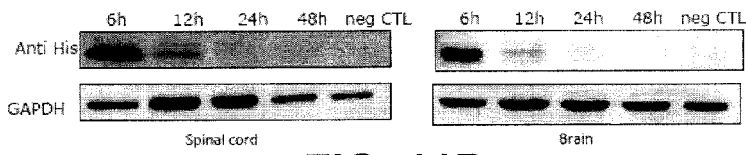

The nanobody was also detected 6, 12 and 24 hours after injection in both brain and spinal cord (FIG. 11D).

To assess whether the SOD1 nanobody could bind overexpressed mutant SOD1, the SOD1 nanobody was injected to a hSOD1$^{G93A}$ mouse, the brain dissected and an immunoprecipitation was performed using an anti-SOD1 antibody. The blot with an anti-His antibody showed that the nanobody and SOD1 were associated and that the nanobody could recognize and bind SOD1 (FIG. 11E).

Figure 12A:
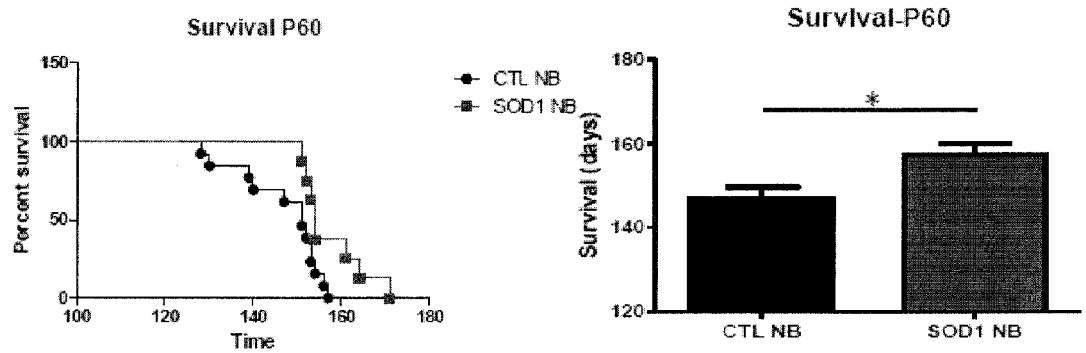
Figure 12B:
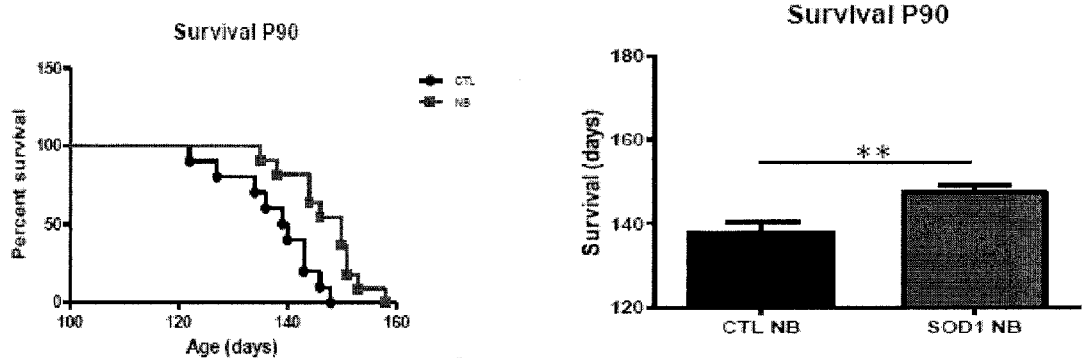
Figure 12C:
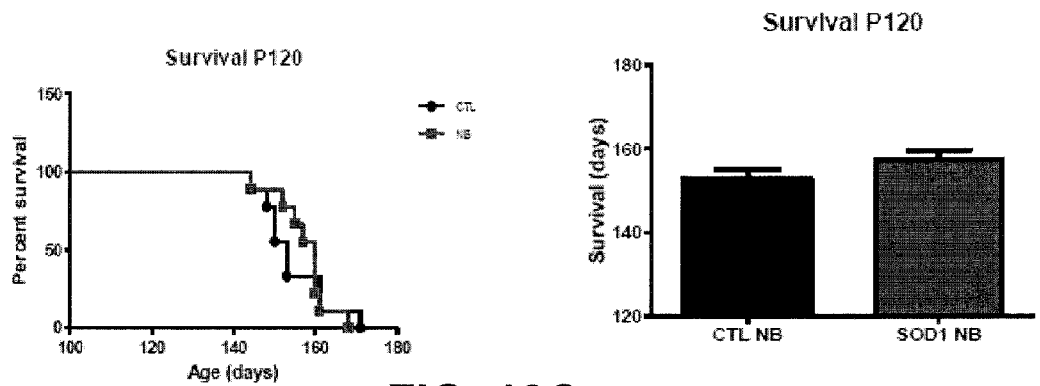

Last, it was desired to test the biological effect of the SOD1 nanobody in this mouse model for ALS. To do so, two different groups of transgenic mice were injected with both control and SOD1 nanobody starting at different time points (FIGS. 12A-12D), testing motor performance and survival. The nanobody was administrated three times a week starting in a pre-symptomatic, symptomatic and end-stage and also daily starting in a symptomatic stage. When the injections started at P60 (FIG. 12A) and P90 (FIG. 12B) and P120 (FIG. 12C), the survival was increased, and the disease onset was delayed also starting at P60 (FIG. 12D).

In all the cases, SOD1 levels or proteins associated with autophagy or the ubiquitin-proteosome system remained the same (data not shown).

The number of MN and neuromuscular junctions (NMJ) of the mice treated from P60 with the control and the SOD1 nanobody was also measured. When the countings were done at P145, the number of small MN (250 to 400 μm$^2$) in the group treated with the SOD1 nanobody was significantly higher than for the control group (FIG. 13A). The number of big MN (>400 μm$^2$) was not significantly different. Besides this fact, the number of NMJ remained the same at this age (FIG. 13B). No toxicity due to the treatment was observed during the experiments.

During all the experiments, the compound muscle axonal potential (CMAP) did not vary between the two groups of injected mice.

As it was described previously, the antibody against the ATP receptor P2X$_4$ recognizes mutant misfolded forms of SOD1.[25] It was also described that these neurotoxic conformers of SOD1 induce astroglia and microglia activation. When brains from mice treated with the control and SOD1 nanobody are immunoprecipitated with the P2X$_4$ antibody, the SOD1 nanobody associated with neurotoxic forms of mutant SOD1 was detected (FIG. 14).

DISCUSSION

ALS is a neurodegenerative disease where around 90% of patients have no familial history and are considered to have the sporadic form. ALS is familial in 10% of patients, and in about 20% of FALS patients, the disease is caused by mutations in the gene encoding SOD1 (see Bento-Abreu[26] and Robberecht and Philips[27] for review). The elimination of mutant SOD1, the primary cause of motor neuron toxicity, is one therapeutic strategy. This has been achieved previously by the viral delivery of RNAi against SOD1,[28, 29] by intracerebroventricular administration of antisense oligonucleotides[30] and by crossbreeding mutant SOD1 mice with mice that express a shRNA against mutant SOD1.[31] Hence, gene silencing holds great promise as a therapy for ALS[32] (and, in fact, for many neurodegenerative diseases). The first clinical studies investigating the feasibility of these approaches in humans are currently underway.

In this study, the objective was to test the potential of nanobodies as a method of decreasing toxicity of mutant SOD1 for the treatment of ALS.

Nanobodies are a unique form of antibodies developed from the discovery that antibodies within camelids can function without light chains and can bind antigens through a single N-terminal (VHH) domain. Harnessing this fact, dromedary and alpaca were immunized with human SOD1 and the VHH of the resulting camelid antibodies was cloned to produce an anti-SOD1 nanobody. In this study, four different isotypes of nanobodies that were selected after consecutive rounds of phage display were identified. Based on preliminary selection, two nanobodies were chosen (one from alpaca and one from dromedary) for further characterization in vitro. The one that had higher affinity was selected for further characterization in vivo.

Although the anti-SOD1 nanobody is not specific for mutant SOD1, the effect of the anti-SOD1 nanobody at disrupting formation of high molecular weight species by mutant SOD1 in vitro, that nanobodies can be expressed in mammalian cells, reducing mutant SOD1 aggregation in different cell lines, that they can rescue related axonopathy induced by mutant SOD1 in zebrafish and also that its beneficial effect in delaying onset and extending lifespan in a mouse model for ALS has been demonstrated herein.

When different cells lines transiently overexpress mutant SOD1, cytoplasmic inclusions are formed. This fact correlates with cell toxicity.[33] After testing SOD1 nanobody expression in transfected cells, it was found that the aggregation, due to transfection with mutant SOD1, is reduced when co-transfecting or treating with the SOD1 nanobody in a dose-dependent way, but not when using a control nanobody. As SOD1 nanobody can be found in the cytosol, also associated with SOD1 and the SOD activity of the cells is decreased when treating with the SOD1 nanobody, it can be concluded that SOD1 nanobody binds SOD1 and prevents it from aggregation. However, further experiments are needed to identify the epitope that the nanobody binds. SOD1 and chaperone levels remain the same, meaning that the SOD1 expression is not altered and the effect is mostly due to the binding of SOD1. No interactions with other elements involved in protein elimination pathways could be seen. In the in vitro experiments, once the aggregates are formed, the presence of the SOD nanobody cannot decrease the number of cells with aggregates, meaning that it could only reduce toxicity when binding oligomeric forms of SOD1.

To test the benefit of the anti-SOD1 nanobody in vivo, mutant SOD1 was injected into zebrafish embryos. Zebrafish is a model of ALS where a toxic gain of function of a mutated SOD1 protein results in a neuronal phenotype.[22] The embryonic nature of this model for a neurodegenerative disease has several major advantages. Treatment of embryos with small compound libraries is more feasible when compared with ALS rodent models and is likely to have more potential than the in vitro models currently used for chemical screening. Another advantage is that drug testing can be performed within 2 days.

It has been found that the SOD1 nanobody could decrease levels of human SOD1 protein following mRNA injection in zebrafish. The fact that in zebrafish embryos the proteosome system is up-regulated might explain why mSOD1 protein levels decrease in the zebrafish model. The beneficial effect of the SOD1 nanobody, injected or added to the water, can be observed in the rescue of the axonal length induced by the injection of mutant SOD1.

One disadvantage of the nanobodies in general is that they are not able to cross the cell membrane. The experiments showed that the SOD1 nanobody is able to enter the cell when it is added to the cell medium. It could be demonstrated that this characteristic is due to the His tag attached to the nanobody, because when it was removed, no inhibition of aggregate formation was found. Although the mechanism was not further investigated, it was hypothesized that the high positive charge of the molecule could favor the interaction with the cell membrane and its internalization.

Next, the SOD1 nanobody was used to treat hSOD1$^{G93A}$ mice, a well-established model to investigate ALS. To optimize the treatment and make possible that small volumes of SOD1 nanobody could reach the CNS with high concentrations, it was administered intracerebroventriculary through a cannula. With one single injection, it could be detected in different areas of the CNS. The detection was possible also after several hours. The injected SOD1 nanobody was able to bind SOD1, although cytoplasmic or extracellular SOD1[34] or between cell types could not be distinguished.

The treatment with SOD1 nanobody significantly inhibits MN death, increases survival and delays disease onset in hSOD1$^{G93A}$ mice. It was demonstrated that SOD1 nanobody binds mutant SOD1, which is associated with ALS,[35] including specific neurotoxic conformers.[25] As no decrease in SOD1 levels or changes in other proteins like chaperones, proteasome or autophagy-related proteins could be observed, the binding of mutant SOD1 and the blocking of its toxic effect appears to be cause of the neuroprotection in these transgenic animals. Since toxicity is thought to be related to the formation of high-molecular-weight complexes and in a final stage, the formation of aggregates,[36,37] it was hypothesized that the SOD1 nanobody could also inhibit the toxicity and the aggregate formation in vivo.

It has also been shown that the SOD1 nanobody is not selective for mutant human SOD1, but can also bind WT human SOD1 and endogenous SOD1. However, this feature does not imply any apparent toxicity or side effects in the experiments, as it was described before.[38,39]

Nanobodies have a wide range of advantages and applications compared with conventional antibodies. Besides the size and the stability, they are easy to produce and also to modify in order to change their properties. The intracerebroventricular infusion of the Fab fragment of a monoclonal antibody against misfolded forms of SOD1,[40] the immunization with mutant SOD1,[41] and the isolation of single-chain fragments of variable regions (scFvs) of antibodies directed against SOD1 and its expression as intrabodies[42] have been published already and they imply a therapeutic approach, but the promising findings herein could have a direct application in ALS therapeutics, not only in SOD1-linked familial cases, where they could have a role, but also in sporadic cases,[1,43,44] where the implication of WT SOD1 in the pathogenesis of ALS has been demonstrated.

REFERENCES

1. Bosco, D. A., et al. Wild-type and mutant SOD1 share an aberrant conformation and a common pathogenic pathway in ALS. *Nature neuroscience* 13, 1396-1403 (2010).
2. Haidet-Phillips, A. M., et al. Astrocytes from familial and sporadic ALS patients are toxic to motor neurons. *Nature biotechnology* 29, 824-828 (2011).
3. Miller, T. W. & Messer, A. Intrabody applications in neurological disorders: progress and future prospects.

*Molecular therapy: the journal of the American Society of Gene Therapy* 12, 394-401 (2005).
4. Saerens, D., Ghassabeh, G. H. & Muyldermans, S. Single-domain antibodies as building blocks for novel therapeutics. *Current opinion in pharmacology* 8, 600-608 (2008).
5. Huang, L., Muyldermans, S. & Saerens, D. Nanobodies®: proficient tools in diagnostics. *Expert review of molecular diagnostics* 10, 777-785 (2010).
6. Revets, H., De Baetselier, P. & Muyldermans, S. Nanobodies as novel agents for cancer therapy. *Expert opinion on biological therapy* 5, 111-124 (2005).
7. De Genst, E. & Dobson, C. M. Nanobodies as structural probes of protein misfolding and fibril formation. *Methods Mol Biol* 911, 533-558 (2012).
8. Muyldermans, S., Atarhouch, T., Saldanha, J., Barbosa, J. A. & Hamers, R. Sequence and structure of VH domain from naturally occurring camel heavy chain immunoglobulins lacking light chains. *Protein engineering* 7, 1129-1135 (1994).
9. Jones, D. R., Taylor, W. A., Bate, C., David, M. & Tayebi, M. A camelid anti-PrP antibody abrogates PrP replication in prion-permissive neuroblastoma cell lines. *PloS one* 5, e9804 (2010).
10. De Genst, E. J., et al. Structure and properties of a complex of alpha-synuclein and a single-domain camelid antibody. *Journal of molecular biology* 402, 326-343 (2010).
11. Emadi, S., et al. Inhibiting aggregation of alpha-synuclein with human single-chain antibody fragments. *Biochemistry* 43, 2871-2878 (2004).
12. Habicht, G., et al. Directed selection of a conformational antibody domain that prevents mature amyloid fibril formation by stabilizing Abeta protofibrils. *Proceedings of the National Academy of Sciences of the United States of America* 104, 19232-19237 (2007).
13. Kasturirangan, S., Boddapati, S. & Sierks, M. R. Engineered proteolytic nanobodies reduce Abeta burden and ameliorate Abeta-induced cytotoxicity. *Biochemistry* 49, 4501-4508 (2010).
14. Colby, D. W., et al. Development of a human light chain variable domain (V(L)) intracellular antibody specific for the amino terminus of huntingtin via yeast surface display. *Journal of molecular biology* 342, 901-912 (2004).
15. Vincke, C. & Muyldermans, S. Introduction to heavy chain antibodies and derived nanobodies. *Methods Mol Biol* 911, 15-26 (2012).
16. Hoogenboom, H. R., et al. Antibody phage display technology and its applications. *Immunotechnology* 4, 1-20 (1998).
17. Winter, G., Griffiths, A. D., Hawkins, R. E. & Hoogenboom, H. R. Making antibodies by phage display technology. *Annu Rev Immunol* 12, 433-455 (1994).
18. Wiseman, T., Williston, S., Brandts, J. F. & Lin, L. N. Rapid measurement of binding constants and heats of binding using a new titration calorimeter. *Analytical biochemistry* 179, 131-137 (1989).
19. Niwa, J., et al. Dorfin ubiquitylates mutant SOD1 and prevents mutant SOD1-mediated neurotoxicity. *The Journal of biological chemistry* 277, 36793-36798 (2002).
20. Cashman, N. R., et al. Neuroblastoma x spinal cord (NSC) hybrid cell lines resemble developing motor neurons. *Developmental dynamics: an official publication of the American Association of Anatomists* 194, 209-221 (1992).
21. Chattopadhyay, M., et al. Initiation and elongation in fibrillation of ALS-linked superoxide dismutase. *Proceedings of the National Academy of Sciences of the United States of America* 105, 18663-18668 (2008).
22. Lemmens, R., et al. Overexpression of mutant superoxide dismutase 1 causes a motor axonopathy in the zebrafish. *Human molecular genetics* 16, 2359-2365 (2007).
23. Laird, A. S., et al. Progranulin is neurotrophic in vivo and protects against a mutant TDP-43 induced axonopathy. *PloS one* 5, e13368 (2010).
24. Van Hoecke, A., et al. EPHA4 is a disease modifier of amyotrophic lateral sclerosis in animal models and in humans. *Nature medicine* 18, 1418-1422 (2012).
25. Hernandez, S., Casanovas, A., Piedrafita, L., Tarabal, O. & Esquerda, J. E. Neurotoxic species of misfolded SOD1G93A recognized by antibodies against the P2X4 subunit of the ATP receptor accumulate in damaged neurons of transgenic animal models of amyotrophic lateral sclerosis. *Journal of neuropathology and experimental neurology* 69, 176-187 (2010).
26. Bento-Abreu, A., Van Damme, P., Van Den Bosch, L. & Robberecht, W. The neurobiology of amyotrophic lateral sclerosis. *Eur J Neurosci* (2010).
27. Robberecht, W. & Philips, T. The changing scene of amyotrophic lateral sclerosis. *Nature reviews. Neuroscience* (2013).
28. Ralph, G. S., et al. Silencing mutant SOD1 using RNAi protects against neurodegeneration and extends survival in an ALS model. *Nature medicine* 11, 429-433 (2005).
29. Raoul, C., et al. Lentiviral-mediated silencing of SOD1 through RNA interference retards disease onset and progression in a mouse model of ALS. *Nature medicine* 11, 423-428 (2005).
30. Smith, R. A., et al. Antisense oligonucleotide therapy for neurodegenerative disease. *The Journal of clinical investigation* 116, 2290-2296 (2006).
31. Xia, X., Zhou, H., Huang, Y. & Xu, Z. Allele-specific RNAi selectively silences mutant SOD1 and achieves significant therapeutic benefit in vivo. *Neurobiology of disease* 23, 578-586 (2006).
32. Maxwell, M. M. RNAi applications in therapy development for neurodegenerative disease. *Curr Pharm Des* 15, 3977-3991 (2009).
33. Turner, B. J., et al. Impaired extracellular secretion of mutant superoxide dismutase 1 associates with neurotoxicity in familial amyotrophic lateral sclerosis. *The Journal of neuroscience: the official journal of the Society for Neuroscience* 25, 108-117 (2005).
34. Urushitani, M., et al. Chromogranin-mediated secretion of mutant superoxide dismutase proteins linked to amyotrophic lateral sclerosis. *Nature neuroscience* 9, 108-118 (2006).
35. Rosen, D. R., et al. Mutations in Cu/Zn superoxide dismutase gene are associated with familial amyotrophic lateral sclerosis. *Nature* 362, 59-62 (1993).
36. Durham, H. D., Roy, J., Dong, L. & Figlewicz, D. A. Aggregation of mutant Cu/Zn superoxide dismutase proteins in a culture model of ALS. *Journal of neuropathology and experimental neurology* 56, 523-530. (1997).
37. Johnston, J. A., Dalton, M. J., Gurney, M. E. & Kopito, R. R. Formation of high molecular weight complexes of mutant Cu, Zn-superoxide dismutase in a mouse model for familial amyotrophic lateral sclerosis. *Proceedings of the National Academy of Sciences of the United States of America* 97, 12571-12576 (2000).

38. Reaume, A. G., et al. Motor neurons in Cu/Zn superoxide dismutase-deficient mice develop normally but exhibit enhanced cell death after axonal injury. *Nature genetics* 13, 43-47. (1996).
39. Bruijn, L. I., et al. Aggregation and motor neuron toxicity of an ALS-linked SOD1 mutant independent from wild-type SOD1. *Science* 281, 1851-1854. (1998).
40. Gros-Louis, F., Soucy, G., Lariviere, R. & Julien, J. P. Intracerebroventricular infusion of monoclonal antibody or its derived Fab fragment against misfolded forms of SOD1 mutant delays mortality in a mouse model of ALS. *Journal of neurochemistry* 113, 1188-1199 (2010).
41. Urushitani, M., Ezzi, S. A. & Julien, J. P. Therapeutic effects of immunization with mutant superoxide dismutase in mice models of amyotrophic lateral sclerosis. *Proceedings of the National Academy of Sciences of the United States of America* 104, 2495-2500 (2007).
42. Ghadge, G. D., Pavlovic, J., Parthasarathy, S. K., Kay, B. K. & Roos, R. P. single-chain variable fragment antibodies block aggregation and toxicity induced by familial ALS-linked mutant forms of SOD1. *Neurobiology of disease* (2013).
43. Guareschi, S., et al. An over-oxidized form of superoxide dismutase found in sporadic amyotrophic lateral sclerosis with bulbar onset shares a toxic mechanism with mutant SOD1. *Proceedings of the National Academy of Sciences of the United States of America* 109, 5074-5079 (2012).
44. Ezzi, S. A., Urushitani, M. & Julien, J. P. Wild-type superoxide dismutase acquires binding and toxic properties of ALS-linked mutant forms through oxidation. *Journal of neurochemistry* 102, 170-178 (2007).

The invention claimed is:

1. A single-domain antibody against the enzyme superoxide dismutase ("SOD1"),
    wherein the single-domain antibody comprises a peptide that binds with both wild-type and mutant SOD 1, wherein the single-domain antibody is able to block fibril formation by SOD 1, and wherein:
    (a) the single-domain antibody comprises a peptide selected from the group consisting of SEQ ID NOS:1-14, or
    (b) the single-domain antibody comprises an amino acid sequence comprising a set of three complementarity determining regions (CDRs), wherein the set of CDRs is selected from:
      i. SEQ ID NOs: 15, 16 and 17;
      ii. SEQ ID NOs: 18, 20 and 21;
      iii. SEQ ID NOs: 19, 20 and 21;
      iv. SEQ ID NOs: 22, 24 and 25;
      v. SEQ ID NOs: 23, 24 and 25; or
      vi. SEQ ID NOs: 26, 27 and 28.

2. The single-domain antibody of claim 1, which is fused to a tag.

3. The single-domain antibody of claim 2, wherein the tag is a His-tag, HA-tag, or Myc-tag.

4. A medicament comprising:
    the single-domain antibody of claim 1, and
    a pharmaceutically acceptable excipient.

5. The single-domain antibody of claim 1, wherein the mutant SOD1 is characterized by an A4V, G93A, and/or G113W mutation.

6. A single-domain antibody against the enzyme superoxide dismutase ("SOD1"),
    wherein the single-domain antibody comprises a peptide selected from the group consisting of SEQ ID NOs:1-14 or
    wherein a complementarity-determining region ("CDR") thereof is selected from SEQ ID NOs:15-28.

7. The single-domain antibody of claim 6, wherein the single-domain antibody comprises a peptide comprising SEQ ID NO:1.

8. The single-domain antibody of claim 6, wherein the single-domain antibody comprises the CDR of SEQ ID NO:16.

9. The single-domain antibody of claim 6, wherein the single-domain antibody comprises the CDR of SEQ ID NO:17.

10. The single-domain antibody of claim 6, wherein the single-domain antibody comprises the CDR of SEQ ID NO:18.

11. The single-domain antibody of claim 6, wherein the single-domain antibody comprises the CDR of SEQ ID NO:19.

12. The single-domain antibody of claim 6, wherein the single-domain antibody comprises the CDR of SEQ ID NO:20.

13. A method of treating amyotrophic lateral sclerosis (ALS) or improving symptoms of ALS in a subject, the method comprising:
    administering the single-domain antibody of claim 1 to the subject.

14. The method according to claim 13, wherein the single-domain antibody is administered intracerebroventricularly.

15. The method according to claim 14, wherein the single-domain antibody is administered through injection or pump to the subject.

* * * * *